US010238738B2

(12) United States Patent
Gray-Owen et al.

(10) Patent No.: US 10,238,738 B2
(45) Date of Patent: Mar. 26, 2019

(54) METHODS OF MODULATING IMMUNE SYSTEM RESPONSES

(71) Applicant: The Governing Council of the University of Toronto, Toronto (CA)

(72) Inventors: Scott Gray-Owen, Oakville (CA); Ryan Gaudet, Toronto (CA); Rebecca Malott, Toronto (CA)

(73) Assignee: The Governing Council of the University of Toronto, Toronto, Ontario (CA)

( * ) Notice: Subject to any disclaimer, the term of this patent is extended or adjusted under 35 U.S.C. 154(b) by 0 days.

(21) Appl. No.: 15/517,605

(22) PCT Filed: Oct. 9, 2015

(86) PCT No.: PCT/CA2015/051026
§ 371 (c)(1),
(2) Date: Apr. 7, 2017

(87) PCT Pub. No.: WO2016/054745
PCT Pub. Date: Apr. 14, 2016

(65) Prior Publication Data
US 2017/0304435 A1 Oct. 26, 2017

Related U.S. Application Data

(60) Provisional application No. 62/062,413, filed on Oct. 10, 2014.

(51) Int. Cl.
| | | |
|---|---|---|
| A61K 45/00 | (2006.01) | |
| A61K 49/00 | (2006.01) | |
| A61K 47/00 | (2006.01) | |
| A61K 39/39 | (2006.01) | |
| A61K 31/7024 | (2006.01) | |
| C07H 11/04 | (2006.01) | |
| G01N 33/50 | (2006.01) | |
| A61K 45/06 | (2006.01) | |
| A61K 39/095 | (2006.01) | |
| C12Q 1/6876 | (2018.01) | |
| C12Q 1/6897 | (2018.01) | |
| A61K 39/00 | (2006.01) | |

(52) U.S. Cl.
CPC .......... *A61K 39/39* (2013.01); *A61K 31/7024* (2013.01); *A61K 39/095* (2013.01); *A61K 45/06* (2013.01); *C07H 11/04* (2013.01); *C12Q 1/6876* (2013.01); *C12Q 1/6897* (2013.01); *G01N 33/502* (2013.01); *A61K 2039/55511* (2013.01); *C12Q 2600/136* (2013.01); *C12Q 2600/178* (2013.01); *Y02A 50/403* (2018.01); *Y02A 50/41* (2018.01); *Y02A 50/412* (2018.01); *Y02A 50/423* (2018.01)

(58) Field of Classification Search
CPC ............................... A61K 39/00; A61K 39/39
USPC .......................... 424/9.1, 9.2, 278.1
See application file for complete search history.

(56) References Cited

FOREIGN PATENT DOCUMENTS

| WO | WO95/30436 A1 | 11/1995 |
| WO | WO02/057449 A1 | 7/2002 |

OTHER PUBLICATIONS

Minoda, Y., et al. Biochemical and Biophysical Research Communications, vol. 344, pp. 1023-1030, 2006.*
Dictionary of Microbiology and Molecular Biology, 3rd edition, eds. Singleton&Sainnsbury, 2006., Title page.*
Dictionary of Microbiology and Molecular Biology, 3rd edition, eds. Singleton&Sainnsbury, 2006., p. 393.*
Brubaker, S. et al., "Microbial metabolite triggers antimicrobial defense", Science, vol. 348, issue 6240, p. 1207-1208, Jun. 12, 2015.
Gaudet, R.G. et al. "Cytosolic detection of the bacterial metabolite HBP activates TIFA-dependent innate immunity", Science, vol. 348, issue 6240, p. 1251-1255, Jun. 12, 2015.
Kneidinger, B. et al. "Biosynthesis pathway of ADP-L-glycero-β-D-manno-Heptose in *Escherichia coli*", Journal of Bacteriology, vol. 184, No. 2, p. 363-369, Jan. 1, 2002.
Huang, Chia-Chi Flora et al. "Intermolecular Binding between TIFA-FHA and TIFA-pT Mediates Tumor Necrosis Factor Alpha Stimulation and NF-kappa B Activation", Molecular and Cellular Biology, vol. 32, No. 14, p. 2664-2673, Jul. 2012.
Malott, Rebecca et al., "Neisseria gonorrhoeae-derived heptose elicits an innate immune response and drives HIV-1 expression", Proceedings of the National Academy of Sciences of the United States of America, vol. 110, No. 25, p. 10234-10239, Jun. 2013.
Matsumura, T. et al., "TIFAB inhibits TIFA, TRAF-interacting protein with a forkhead-associated domain", Biochemical and Biophysical Research Communications, vol. 317, No. 1, p. 230-234, Apr. 2004.

* cited by examiner

*Primary Examiner* — Rodney P Swartz
(74) *Attorney, Agent, or Firm* — Bereskin & Parr LLP/S.E.N.C.R.L., s.r.l.; Micheline Gravelle

(57) ABSTRACT

Novel methods and uses for modulating immune responses are provided. The methods and uses involve the use of a TIFA activator such heptose-1,7-5 bisphosphate or an analog or derivative thereof. The methods may be used to activate, inhibit or otherwise modify an immune response so as to either prevent or treat infectious or inflammatory diseases or cancer. Also provided are methods to identify compounds capable of modulating immune responses.

10 Claims, 22 Drawing Sheets
Specification includes a Sequence Listing.

METHODS OF MODULATING IMMUNE SYSTEM RESPONSES

The present application is the national phase entry application of PCT/CA2015/051026, filed Oct. 9, 2015 (which designates the U.S.), which claims the benefit of priority from U.S. provisional application No. 62/062,413 filed Oct. 10, 2014, the contents of both of which are incorporated herein by reference in their entirety.

INCORPORATION OF SEQUENCE LISTING

A computer readable form of the Sequence Listing "2223-P47263US01_SequenceListing.txt" (16,384 bytes), submitted via EFS-WEB and created on Mar. 22, 2017, is herein incorporated by reference.

FIELD OF THE DISCLOSURE

The present disclosure relates to methods and uses for modulating immune responses in a subject. The methods and uses are useful in the prevention and treatment of infectious diseases, the prevention and treatment of cancers, as well as the treatment of immune and inflammatory disorders.

BACKGROUND OF THE DISCLOSURE

The following paragraphs are intended to introduce the reader to the more detailed description that follows and not to define or limit the claimed subject matter of the present disclosure.

The immune system provides protection against infectious agents, including bacteria, viruses, fungi, and parasites. A substantial number of medical conditions are associated with a compromised immune system and an increased susceptibility to infectious agents. Thus, for example, patients undergoing surgery, radiation or chemotherapy, and those suffering from auto immune diseases and diseases interfering with a normal metabolic immune response, such as HIV (AIDS), are all at a heightened risk of developing pathological conditions resulting from infection. While pharmaceuticals—antibiotics, such as ampicillin, tetracycline and quinolones, for example, in the case of bacterial infections—offer treatment options, resistance of the infectious agent to these pharmaceuticals is an increasingly significant concern. Therefore, there is need for immune activating or modulating strategies to induce responses better able to prevent or combat infection. Furthermore, vaccines preventing or treating infection by many microbial organisms have been developed, however there is an ongoing need for additional vaccine formulations, as the immune stimulatory profile of known vaccine formulations is frequently suboptimal. Vaccines have also been proposed to help the immune system target cancerous cells or tissues, however there is a need to improve the immune response so that it can more effectively combat the cancer. Finally, there is ongoing need to alter pathogenic immune responses, and particularly pathogenic inflammatory responses, to reduce disease symptoms and/or progression.

Therefore there is a need in the art to develop further treatment and prevention options against infections caused by infectious agents, cancerous cells and immune or inflammatory diseases.

SUMMARY OF THE DISCLOSURE

The present disclosure provides novel methods and uses for modulating immune responses in a subject.

The inventors have shown that heptose-1,7-biphosphate (HBP) activates the tumor necrosis factor (TNF) receptor-associated factor (TRAF) interacting forkhead associated protein A (TIFA). The inventors have also shown that HBP can modulate an immune response.

Accordingly, in one aspect, the present disclosure provides a method of modulating an immune response comprising administering an effective amount of TIFA activator to a subject in need thereof. In one embodiment, the TIFA activator is heptose-1,7-bisphosphate or an analogue or derivative thereof.

Accordingly, the present disclosure provides, in at least one embodiment, a method of modulating an immune response in a subject comprising administering an effective amount of heptose-1,7-bisphosphate or an analogue or derivative thereof to a subject in need thereof. The disclosure also provides a use of heptose-1,7-bisphosphate or an analogue or derivative thereof to modulate an immune response. The disclosure further provides heptose-1,7-bisphosphate or an analogue or derivative thereof for use in modulating an immune response.

The present disclosure provides, in a further embodiment, a method of modulating an inflammatory response in a subject comprising administering an effective amount of heptose-1,7-bisphosphate or an analogue or derivative thereof to a subject in need thereof. The disclosure also provides a use of heptose-1,7-bisphosphate or an analogue or derivative thereof to modulate an inflammatory response. The disclosure further provides heptose-1,7-bisphosphate or an analogue or derivative thereof for use in modulating an inflammatory response.

The present disclosure provides, in a further embodiment, a method of modulating an immune response by administering an effective amount of heptose-1,7-bisphosphate or an analogue or derivative thereof in combination with an immunogen, to a subject in need thereof. The disclosure also provides a use of heptose-1,7-bisphosphate or an analogue or derivative thereof in combination with an immunogen to modulate an immune response. The disclosure further provides heptose-1,7-bisphosphate or an analogue or derivative thereof in combination with an immunogen for use in modulating an immune response.

The present disclosure further provides a pharmaceutical composition for modulating an immune response, an inflammatory response, or for administration in combination with an immunogen for the purpose of preventing, treating, ameliorating, or inhibiting an injury, disease, disorder or condition by administering an effective amount of heptose-1,7-bisphosphate or an analogue or derivative thereof to a subject in need thereof.

The present disclosure further provides a method for stimulating a molecular receptor of heptose-1,7-bisphosphate capable of molecular signaling upon interaction with heptose-1,7-bisphosphate, by contacting the heptose-1,7-bisphosphate with the molecular receptor under conditions that permit activation of the TRAF-interacting forkhead associated protein A ("TIFA"). The method, in accordance herewith, may be performed in vitro or in vivo. The present disclosure still further provides methods for selecting a compound capable of modulating an immune response in a subject in need thereof by activating TIFA-dependent signal cascades. Thus the disclosure provides a method for selecting a compound capable of effecting a TIFA signaling response comprising:

(a) providing a test compound with the potential to effect TIFA in a manner that results in a TIFA signaling response;

(b) comparing in a functional assay the effect of the test compound on TIFA with a control; and (c) selecting a test compound exhibiting an effect on the signaling response of TIFA for further evaluation.

In certain embodiments, the compound is a polynucleotide. In certain embodiments the control comprises performance of the functional assay using a cell that does not express TIFA as a negative control. In other embodiments, the control comprises HBP as a positive control.

Other features and advantages of the present disclosure will become apparent from the following detailed description. It should be understood, however, that the detailed description, while indicating preferred embodiments of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described in relation to its Figures. The Figures provided herein are provided for illustration purposes and are not intended to limit the present disclosure.

(FIG. 1(b), NF-κB luciferase activity in 293T cells treated with purified culture supernatants prepared from *N. meningitidis* of the indicated genotype. FIG. 1(c), Silver stain of LOS extracts from indicated *N. meningitidis* isogenic strains. FIG. 1(d), FIG. 1(e) NF-κB luciferase activity in 293T cells treated with the product of in vitro reactions containing combinations of sedoheptulose-7-phosphate (S7P), His-tag purified GmhA and HldA (FIG. 1(d)), and then incubated with or without His-tag purified GmhB (FIG. 1(e)).

FIG. 2(b), qRT-PCR analysis of pro-inflammatory gene transcription in Jurkat 1G5 cells treated with purified HBP containing supernatants, flagellin, or TNFα for the indicated times. FIG. 2(c), Binding and kinetics of the indicated NF-κB subunits from nuclear extracts from Jurkat T cells to consensus oligonucleotides by ELISA following treatment with HBP containing supernatants or flagellin.

FIG. 3(b), NF-κB luciferase activity in 293T cells treated with HBP containing or deficient (ΔhldA) supernatants, or TNFα in the presence of vehicle (DMSO), dynasore (Dyn), or cytochalasin D (Cyto D). FIG. 3(c), qRT-PCR analysis of THP-1 macrophages treated with synthetic HBP (sHBP), PAM3CSK4 (PAM3), or flagellin (FLAG) for 4 hr, expressed as fold increase relative to untreated after normalization to GAPDH. Data represent ≥3 independent experiments performed in duplicate. All error bars±s.e.m. *P<0.05, **P<0.01 by ANOVA.

FIG. 4(b), NF-κB luciferase activity in 293T cells transfected with soluble lysates from *N. meningitis* or *E. coli* lacking the indicated genes in the ADP-heptose biosynthesis pathway. FIG. 4(c), Silver stain of LPS extracts from *E. coli* mutants showing all 3 *E. coli* mutants have the same "deep rough" phenotype. Data represent ≥3 independent experiments performed in duplicate. All error bars±s.e.m.

FIG. 5(b) NF-κB luciferase activity in 293T cells treated with soluble lysates or culture supernatants. FIG. 5(c) prepared from *E. coli* (BL21) cells expressing the indicated *N. meningitis* genes from an IPTG-inducible vector. Data represent A independent experiments performed in duplicate. All error bars±s.e.m.

FIG. 7 (b), qRT-PCR analysis of the knockdown efficiency of RIP2 in 293T cells. FIG. 7 (c), shRNA Knockdown (top) and knockdown efficiencies (bottom) of MyD88, STING, CARD9, RIP2, or MAVS in THP-1 differentiated macrophages, then treated with HBP, LPS, c-di-GMP, MDP, or dsRNA and IL-6 or IL-8 measured.

FIG. 8 (d) ELISA of IL-6, IL-8, IL-23 or IFN-β production in primary human macrophages infected with *N. meningitidis* ΔhldA or ΔgmhB (6 hr). FIG. 8 (e), FIG. 8 (f) KC levels in mouse serum and air pouch washes (AP) (FIG. 8 (e)) or neutrophil counts in the air pouch (FIG. 8 (f)) following injection of HBP-containing or deficient purified culture supernatants from *N. gonorrhoeae* into previously raised dorsal pouches (n=6) (3 hr). FIGS. 8 (a), (b), (d) are representative of 3 different donors. FIG. 8 (c) represent 3 independent experiments. All error bars±s.e.m. *P<0.05 by t-test.

FIG. 11 (C) optimization of the RNAi screen by titrating in an NFKB1 targeting shRNA into the 78 000 shRNA library at the indicated percentage, transducing Jurkat RG5 cells at an MOI=0.3, and monitoring the change in resulting DsRed negative cells following treatment with HBP. FIG. 11 (D) Flow cytometry analysis of DsRed expression (a readout of HIV promoter activity) in Jurkat T cells following treatment with HBP.

FIG. 12(*b*), Knockdown of TIFA abrogates HBP-mediated DsRed expression. Jurkat RG5 reporter cells were transduced with one of two TIFA targeting shRNAs (red histograms), or a scrambled shRNA (black histograms) and either left untreated (grey filled histogram), or treated with HBP, TNFα, or flagellin. DsRed expression was determined 48 hr later using FACS. FIG. 12(*c*), Knockdown of TIFA abrogates the HBP induced pro-inflammatory transcriptional response. qRT-PCR analysis of previously identified (see FIG. 2) HBP-unregulated genes in Jurkat cells transduced with shRNAs targeting TIFA, RelA, or scrambled, then treated with HBP, TNFα or flagellin for 2 hours. FIG. 12(*d*) Luciferase activity of Jurkat 1G5 cells transduced with lentiviral MSCV-driven FLAG-TIFA, or empty vector, and treated with shRNAs targeting the TIFA-untranslated region (UTR), or the coding sequence (CDS) then treated with HBP (6 hr). FIG. 12(*e*), NF-κB luciferase activity following TIFA knockdown in 293T cells and treated with HBP containing supernatants, TNFα, or transfected with the indicated Gram-negative lysate. Gray-bars represent stable expression of FLAG-TIFA and knockdown with the TIFA-untranslated region (UTR) targeting shRNA. Data are from 3 independent experiments (error bars s.e.m of three replicates). **P<0.01.

FIG. 16(*b*), Immunofluorescence microscopy in 293T cells of the formation of a TIFA-TRAF6 complex with or without HBP (3 hr), scale bars, 10 μm. Data are representative of ≥ independent experiments.

FIG. 17(*b*), TIFA knockdown and TRAF6 IP analysis of the TIFA-TRAF6-ubiquitin complex in Jurkat cells treated with HBP or flagellin. Data are representative of ≥2 independent experiments.

FIG. 18(*b*), qRT-PCR assessment of the knockdown efficiency of IRAK1, IRAK2, or IRAK4 shRNA. Data were normalized to GAPDH, and expressed as a percentage of the mRNA observed in cells not expressing an shRNA.

FIG. 19(*b*), LTR-driven luciferase activity in Jurkat 1G5 cells stably expressing FLAG-TIFA wild type (Wt), T9A, G50E S66A, or E178A, then treated with srambled shRNA, or shRNA specific for the TIFA 3' UTR, (UTR) or coding sequence (CDS) and treated with HBP (6 hr). FIG. 19(*c*), Immuno-precipitaiton (IP) analysis of the HBP-induced TIFA-TRAF6 interaction in Jurkat cells stably expressing FLAG-TIFA wildtype (wt), T9A, G50E S66A, or E178A, then treated with TIFA 3' UTR specific shRNA. FIG. 19(*d*), Co-transfection of 293T cells with a HIV-1 LTR-DsRed construct, and pMSCV-FLAG-TIFA of the indicated genotype and FACS analysis of the number DsRed positive cells after 36 hours. FIG. 19(*b*), Represent 3 independent experiments (error bars s.e.m.), FIG. 19(*c*), FIG. 19(*d*), are representative of ≥3 independent experiments.

FIG. 20(b), clear native PAGE and Immunoblot analysis of FLAG-TIFA oligomerization in HBP treated Jurkat cells. Lysates were treated with or without λ protein phosphatase (λPPAse) before running the gel. FIG. 20(c), blue native PAGE analysis of Jurkat cells stably expressing FLAG-TIFA, a TIFA UTR-targeting shRNA, and treated with HBP for the indicated time. Estimated molecular weight markers based on the NativeMARK™ protein standards are indicated on the right. Data are representative are representative of ≥2 independent experiments.

DETAILED DESCRIPTION OF THE DISCLOSURE

Figure 1:
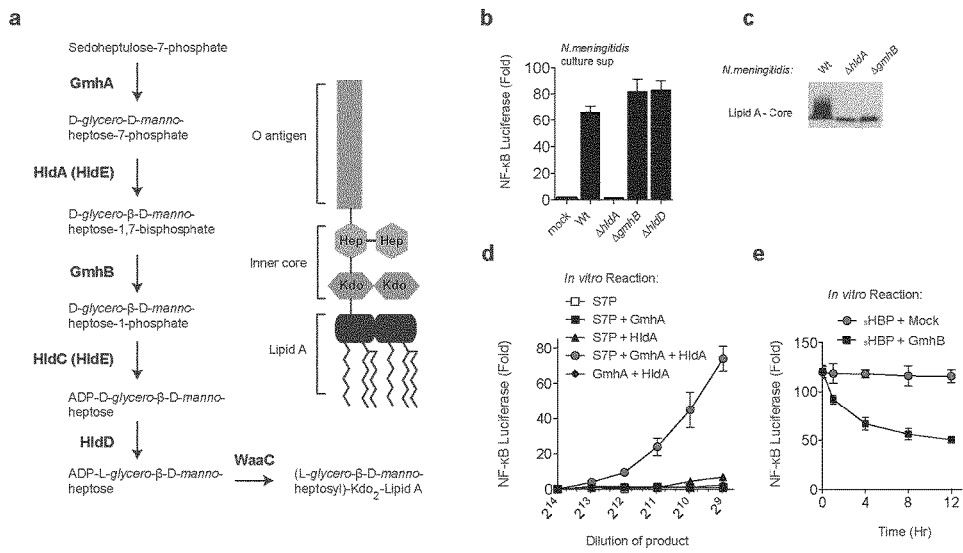
FIG. 1 Shown in FIG. 1(a) is a schematic depiction of the ADP-heptose (ADP-hep) biosynthetic pathway in Gram-negative bacteria. Supplied by the pentose phosphate pathway, sedoheptulose-7-phosphate is converted to ADP-L-glycero-D-manno-heptose (ADP-hep), the precursor for the synthesis of the inner core of LOS and LPS in five steps (Kneidinger et al., 2002). *Neisseria* enzymes are indicated in bold. *E. coli* enzymes, when different than *Neisseria*, are in parenthesis.

Various compositions and methods will be described below to provide an example of an embodiment of each claimed subject matter. No embodiment described below limits any claimed subject matter and any claimed subject matter may cover methods, processes, compositions or systems that differ from those described below. The claimed subject matter is not limited to compositions or methods having all of the features of any one composition, method, system or process described below or to features common to multiple or all of the compositions, systems or methods described below. It is possible that a composition, system, method or process described below is not an embodiment of any claimed subject matter. Any subject matter disclosed in a composition, system, method or process described below that is not claimed in this document may be the subject matter of another protective instrument, for example, a continuing patent application, and the applicants, inventors or owners do not intend to abandon, disclaim or dedicate to the public any such subject matter by its disclosure in this document.

It should be noted that terms of degree such as "substantially", "essentially" "about" and "approximately" as used herein mean a reasonable amount of deviation of the modified term such that the end result is not significantly changed. These terms of degree should be construed as including a deviation of the modified term if this deviation would not negate the meaning of the term it modifies.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

As used in this specification and the appended claims, the singular forms "a", "an", and "the" include plural referents unless the content clearly dictates otherwise. Thus, for example, reference to "an immunogen" includes a mixture of two or more such agents, reference to "a polypeptide" includes reference to mixtures of two or more polypeptides, reference to "a cell" includes two or more such cells, and the like.

All publications, patents and patent applications are herein incorporated by reference in their entirety to the same extent as if each individual publication.

As hereinbefore mentioned, the present disclosure provides, in at least one embodiment, a method of modulating an immune response in a subject comprising administering an effective amount of heptose-1,7-bisphosphate to a subject in need thereof. In one aspect, the method involves the use of heptose-1,7-bisphosphate to activate the "TRAF-interacting forkhead associated protein A" or "TIFA". The methods are useful in that they permit the modulation of the immune system of a subject in need thereof.

Terms and Definitions

Unless defined otherwise, all technical and scientific terms used herein shall have the same meaning as commonly understood by one of ordinary skill in the art to which the disclosure pertains. The following terms shall be understood to have the following meanings.

Figure 22:
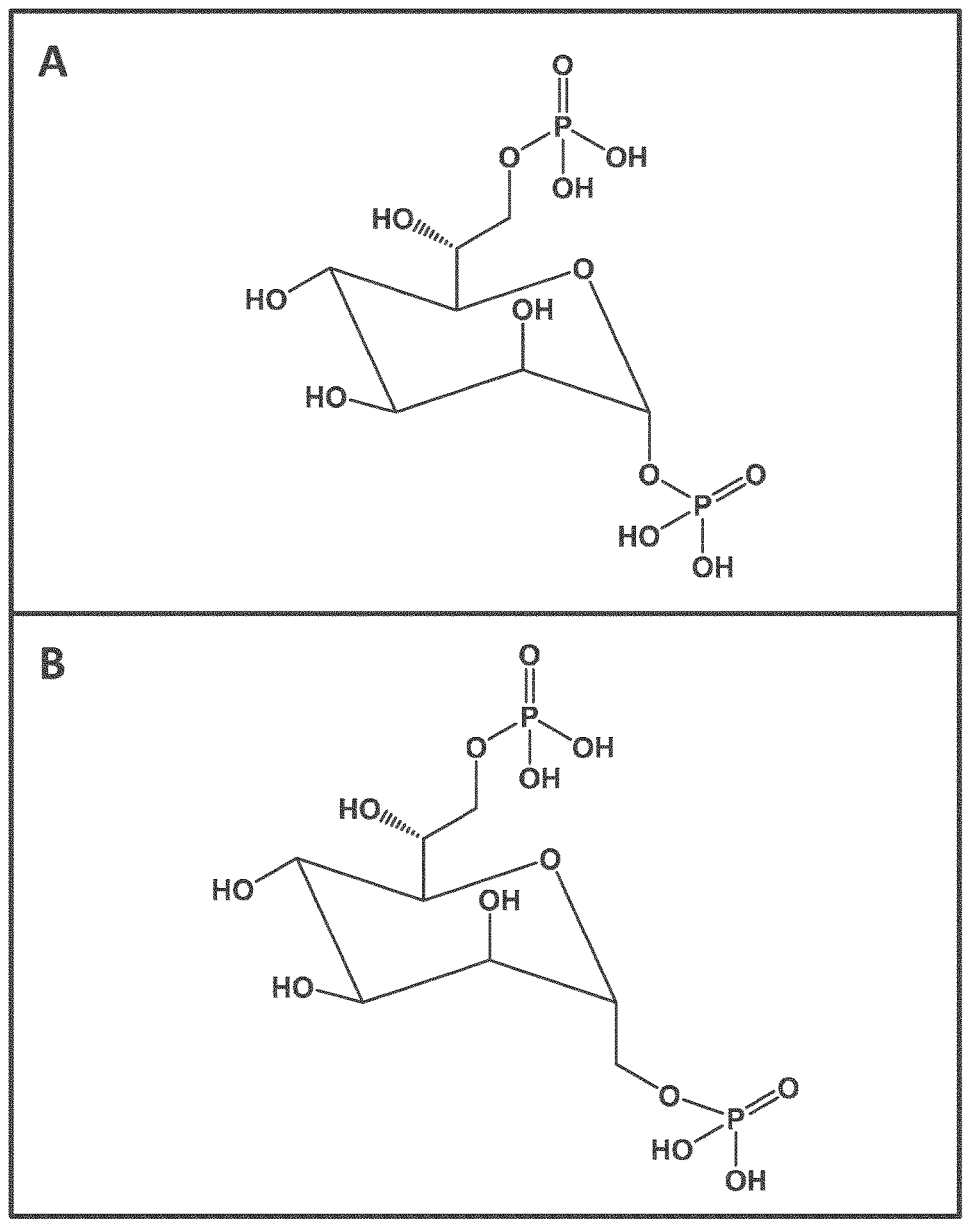
FIG. 22. Shown is the chemical structures of D-glycero-D-manno-heptose-1a 7 bis-phosphate, notably D-glycero-D-manno-heptose-1α 7 bis-phosphate (FIG. 22(A)) and D-glycero-D-manno-heptose-1β 7 bis-phosphate (FIG. 22(B)).

The terms "heptose-1,7-bisphosphate" or "HBP" as may be interchangeably used herein, refer to chemical compounds having the structural formula set forth in FIG. 22, and includes D-glycerol-D-manno-heptose-1α 7 bis-phosphate (FIG. 22A) and D-glycerol-D-manno-heptose-1β 7 bis-phosphate (FIG. 22B) as well as any analogues or derivatives thereof. Such analogues or derivatives will also be useful in modulating an immune response.

The term "modulate" as used herein in connection with an immune or inflammatory response, is intended to refer to any qualitative or quantitative alteration in the immune or inflammatory response in a subject, including, without limitation, any stimulation or activation, or any reduction or inhibition of an immune or inflammatory response, and further also including an alteration in the type of immune response, e.g. an immune response altering from being a substantially humoral immune or inflammatory response to a substantially cell mediated immune response, or vice versa.

The interchangeably herein used terms "TRAF-interacting forkhead-associated protein A", "TIFA", "TIFA Protein", and "TIFA Polypeptide" refer to any and all TIFA polypeptides, including those set forth in SEQ.ID.NO: 2, and those comprising a sequence of amino acid residues which (i) are substantially identical to the amino acid sequences constituting any TIFA protein set forth herein; (ii) are encoded by a nucleic acid sequence capable of hybridizing under at least moderately stringent conditions to any nucleic acid sequence encoding any TIFA protein set forth herein or capable of hybridizing under at least moderately stringent conditions to any nucleic acid sequence encoding any TIFA protein set forth herein, but for the use of synonymous codons. The term includes the human TIFA and its homologues expressed by vertebrates, and particularly those homologues expressed by mammals. The terms further include any recombinantly-derived TIFA polypeptides encoded by cDNA copies of the natural polynucleotide sequence encoding TIFA.

The term "TRAF-interacting forkhead-associated protein A activator" or "TIFA activator" refers to any molecule that can activate TIFA. Activation can be assessed by measuring levels of the TIFA protein or nucleic acids encoding the TIFA protein. Activation can also be assessed by measuring activation of downstream molecules that are activated by TIFA such as NF-κB.

The herein interchangeably used terms "polynucleotide encoding a TRAF forkhead-associated protein A"; "polynucleotide encoding a TIFA polypeptide"; and "polynucleotide encoding a TIFA protein" refer to any and all polynucleotides encoding a TIFA polypeptide, including any TIFA polypeptide and any nucleic acid sequences that encode recombinantly-derived TIFA polypeptides, including the polynucleotides set forth in SEQ.ID.NO:1. Polynucleotides encoding a TIFA polypeptide further include any and all polynucleotides which (i) encode polypeptides that are substantially identical to the TIFA polypeptide sequences set forth herein; or (ii) hybridize to any TIFA polynucleotides set forth herein under at least moderately stringent hybridization conditions or which would hybridize thereto under at least moderately stringent conditions but for the use of synonymous codons. The term is further also is meant to include recombinantly-derived TIFAs containing polypeptides used to monitor expression and/or signaling by TIFA protein, including but not limited to epitope tags that can be recognized by epitope sequence-specific antibodies.

By the term "substantially identical" it is meant that two polypeptide sequences preferably are at least 50% identical, and more preferably are at least 85% identical and most preferably at least 95% identical, for example 96%, 97%, 98% or 99% identical. In order to determine the percentage of identity between two polypeptide sequences the amino acid sequences of such two sequences are aligned, using for example the alignment method of Needleman and Wunsch (Needleman S B, Wunsch C D. 1970. A general method applicable to the search for similarities in the amino acid sequence of two proteins. Journal of Molecular Biology 48:443-453), as revised by Smith and Waterman (Smith T F, Waterman, M S. 1981. Comparison of biosequences. Advances in Applied Mathematics 2:482-489) so that the highest order match is obtained between the two sequences and the number of identical amino acids is determined between the two sequences. A preferred, broadly applicable, method for accurately aligning two polypeptides involves the Clustal W algorithm (Thompson J D, Higgins D G, Gibson T J. 1994. CLUSTAL W: improving the sensitivity of progressive multiple sequence alignment through sequence weighting, position-specific gap penalties and weight matrix choice. Nucleic Acids Research 22:4673-4680.), employed with the BLOSUM 62 scoring matrix (Henikoff S, Henikoff J G. 1992. Amino acid substitution matrices from protein blocks. Proc Natl Acad Sci USA 89:10915-10919) using a gap opening penalty of 10 and a gap extension penalty of 0.1. This enables identification of high scoring alignments between two sequences, wherein at least 50% of the total length of one of the two sequences is involved in the alignment. Methods to calculate the percentage identity between two aligned amino acid sequences are generally art recognized and include, for example, those described by Carillo and Lipton (Carrillo H, and D. Lipman. 1989. The multiple sequence alignment problem in biology. SIAM Journal on Applied Mathematics 48:1073-1082), and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux J, Haeberli P, Smithies O. 1984. A comprehensive set of sequence analysis programs for the VAX. Nucleic acids research 12:387-395), BLASTP, BLASTN and FASTA (Altschul S F, Gish W, Miller W, Myers E W, Lipman D J. 1990. Basic local alignment search tool. Journal of Molecular Biology 215: 403-410).

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.-16.6 (Log 10 [Na+])+0.41(% (G+C)-600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations, those skilled in the art will be able to readily select appropriate hybridization conditions. In preferred embodiments, stringent hybridization conditions are selected. By way of example, the following conditions may be employed to achieve stringent hybridization: hybridization at 5× sodium chloride/sodium citrate (SSC)/5×Denhardt's solution/1.0% SDS at Tm (based on the above equation) −5° C., followed by a wash of 0.2×SSC/0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Green and Sambrook, Molecular Cloning, a Laboratory Manual, Cold Spring Harbor Laboratory Press, 2012.

The term "chimeric" as used herein in the context of polynucleotides refers to at least two linked polynucleotides which are not naturally linked. Chimeric nucleic polynucleotides include linked polynucleotides of different natural origins. For example, a polynucleotide constituting an *E. coli* bacterial promoter linked to a polynucleotide encoding a TIFA polypeptide is considered chimeric. In addition chimeric polynucleotides may have the same natural origin but are not naturally linked. For example, a polynucleotide constituting a promoter obtained from a particular cell-type may be linked to a polynucleotide encoding a polypeptide obtained from that same cell-type, but not normally linked to the polynucleotide constituting the promoter. Chimeric polynucleotides also include polynucleotides comprising any naturally occurring polynucleotide linked to any non-naturally occurring polynucleotide.

The terms "immunogen" and "immunogenic composition", as interchangeably used herein, are used in their broadest sense to refer to a molecule which contains one or more epitopes that will stimulate the immune response in a host organism to generate a cellular immunogen-specific immune response, or a humoral antibody response. Immunogens include antigens, proteins, polypeptides, peptides, immunogenic protein fragments and immunogenic carbohydrates.

The term "vertebrate subject" refers to any member of the subphylum cordata, particularly mammals, including, without limitation, humans and other primates. The term does not denote a particular age. Thus, both newborn, infant, child and adult individuals are intended to be covered.

The terms "vaccine" and "vaccine composition", as interchangeably used herein, refer to any pharmaceutical composition containing an immunogen, which composition can be used to prevent or treat a disease or condition in a subject. The terms thus encompass subunit vaccines, i.e., vaccine compositions containing immunogens which are separate and discrete from a whole organism with which the immunogen is associated in nature.

Methods and Uses

The inventors have shown that heptose-1,7-bisphosphate activates the TRAF-interacting forkhead associated protein A (TIFA). The inventors have also shown that HBP can modulate an immune response.

Accordingly, in one aspect, the present disclosure provides a method of modulating an immune response comprising administering an effective amount of TIFA activator to a subject in need thereof. In one embodiment, the TIFA activator is heptose-1,7-bisphosphate or an analogue or derivative thereof. In a specific embodiment, the TIFA activator is heptose-1,7-bisphosphate.

In another embodiment, the present disclosure provides a method of modulating an immune response in a subject comprising administering an effective amount of heptose-1,7-bisphosphate or an analogue or derivative thereof to a subject in need thereof. The disclosure also provides a use of heptose-1,7-bisphosphate or an analogue or derivative thereof to modulate an immune response. The disclosure further provides heptose-1,7-bisphosphate for use in modulating an immune response. The disclosure yet also provides a use of heptose-1,7-bisphosphate or an analogue or derivative thereof in the manufacture of a medicament for modulating an immune response. In a specific embodiment, heptose-1,7-bisphosphate is used.

Heptose-1,7-bisphosphate that may be used in accordance herewith are any preparations and formulations comprising more or less pure heptose-1,7-bisphosphate capable of modulating an immune response in an individual, including D-glycerol-D-manno-heptose-1α 7 bisphosphate and D-glycerol-D-manno-heptose-1β 7 bisphosphate, analogues, derivatives and mixtures thereof. Heptose-1,7-bisphosphate may be synthesized chemically from commonly known and readily commercially obtainable chemical precursor constituents, or it may be extracted and obtained in more or less pure preparations from microbial sources. These microbial sources may be natural or genetically modified in order to enhance the production of heptose-1,7-bisphosphate, such as by the introduction of mutations in the gene encoding the enzyme GmhB, or deletion of the GmhB gene, which leads to the accumulation of heptose-1,7-bisphosphate in the cell or culture supernatant, or alternatively, by over expressing the *Neisseria* gene HldA in *E. coli* leading to increased synthesis of heptose-1,7-bisphosphate. Alternatively, heptose-1,7-bisphosphate may be prepared biosynthetically using, for example, sedoheptulose-7-phosphate, which may be purchased commercially, for example from Sigma, as a substrate for preparation of the enzymes GmhA and HldA, obtained from, for example, *Neisseria meningitis*, or GmhA and HldA, obtained from, for example, *Escherichia coli*. In this regard it is particularly beneficial to clone and express polynucleotides encoding gmhA (SEQ.ID.NO: 3 or SEQ.ID.NO:4) and either the *Neisseria*-derived hldA (SEQ.ID NO:5) or *Escherichia coli*-derived hldA (SEQ.ID NO:6, so as to recombinantly express GmhA and either the *neisserial* HldA or *E. coli* HldE in, for example, *Escherichia coli*. Incubation of sedoheptulose-7-phosphate with GmhA results in enzymatic conversion of sedoheptulose-7-phosphate to D-glycerol-D-manno-heptose-7-phosphate, which in turn in the presence of HldA is converted into heptose-1,7-bisphosphate. The foregoing biosynthesis of heptose-1,7-bisphosphate is further described in Example 1 hereto.

Methods of administration that may be used in accordance herewith include, but are not limited to, parenteral (e.g. intravenous, intraperitoneal, intramuscular, subcutaneous), mucosal (e.g. oral, intranasal, buccal, vaginal, rectal, intraocular), intrathecal, oral, topical and intradermal routes. Administration may be local or systemic. The subject in need of administration may be in need thereof for the purpose of preventing, treating, ameliorating, or inhibiting an injury, disease, disorder or condition.

The inventors have shown that delivering HBP directly into a cell enhances the activity of HBP. Accordingly, in one embodiment the the TIFA activator such as heptose-1,7-bisphosphate or an analogue or derivative thereof is delivered directly into the cell.

An effective amount of the TIFA activator such as heptose-1,7-bisphosphate or an analogue or derivative thereof in accordance herewith is intended to refer to an amount that is sufficient for preventing, treating, ameliorating, an injury, disease, disorder, indication or condition. The effective amount may vary and typically depends on a variety of factors such as, the injury, disease, disorder indication or condition, the route or mode of administration, the administration regimen, the severity of the condition, the subject's general health, age, and weight, and dosage of the formulation. In general a person of skill in the art will be able to readily determine the effective amount.

In the present disclosure, the subject encompasses any animal subject, including any vertebrate subject, including any human subject, that requires immunomodulation, including for the purposes of prevention of a disease, or for treatment of an infectious, immune or inflammatory disease or cancer.

In general, the methods of the present disclosure can be used to therapeutically or prophylactically treat any subjects for which increased activation of the immune system or an altered immune response would be beneficial. This includes, but is not restricted to a subject suffering from a condition which deleteriously affects the immune system, including any subject at a heightened risk of infection or actually infected, for example due to surgery or imminent surgery, injury, illness, radiation or chemotherapy, and any subject suffering from auto immune diseases, inflammatory disorders, cancers, and diseases which cause the normal metabolic immune response to be compromised, such as HIV (AIDS).

In accordance with the present disclosure, the immune response is modulated upon delivery of the TIFA activator such as heptose-1,7-bisphosphate or an analogue or derivative thereof. In certain embodiments, the immune response is activated, stimulated or enhanced. In other embodiments, the immune response is reduced or suppressed. In other embodiments, the immune response is altered, for example by changing an immune response from one that is predominantly humoral to one that is predominantly cell-mediated or vice versa.

The present disclosure provides, in a further embodiment, a method of modulating an inflammatory response in a subject comprising administering an effective amount of a TIFA activator such as heptose-1,7-bisphosphate or an analogue or derivative thereof to a subject in need thereof. The disclosure also provides a use of a TIFA activator such as heptose-1,7-bisphosphate or an analogue or derivative thereof to modulate an inflammatory response. The disclosure further provides a TIFA activator such as heptose-1,7-bisphosphate or an analogue or derivative thereof for use in modulating an inflammatory response. The disclosure yet also provides a use of a TIFA activator such as heptose-1, 7-bisphosphate or an analogue or derivative thereof in the manufacture of a medicament to modulate an inflammatory response.

The inventors have shown that a Gram negative bacterium that has been modified so it does not express HBP is less immunogenic and less inflammatory than a normal bacteria that does express HBP. Such modified bacteria can be used as a live vaccine strain. Accordingly, the present disclosure includes a method of reducing inflammation comprising administering an effective amount of a bacteria that does not express HBP. The disclosure also includes a use of a bacteria that does not express HBP to reduce an inflammation. The disclosure yet also provides a bacteria that does not express HBP to reduce an inflammation. The disclosure further provides a use of a bacteria that does not express HBP in the manufacture of a medicament to reduce an inflammation.

In accordance with this embodiment, the administration of a TIFA activator such as heptose-1,7-bisphosphate results in the modulation of the inflammatory disorder of a subject. Such inflammatory disorders include, but are not limited to, acute and chronic inflammation disorders, including, without limitation, atherosclerosis, allergies, asthma, inflammatory bowel disease and myopathies.

The present disclosure provides, in a further embodiment, a method of modulating an immune response by administering an effective amount of a TIFA activator such as heptose-1,7-bisphosphate to a subject in need thereof in combination with an immunogen or antigen against which one wishes to stimulate an immune response. Delivery in combination with an immunogen includes co-administration of heptose-1,7-bisphosphate and the immunogen or administration of heptose-1,7-bisphosphate, separately from the immunogen, e.g. prior or post delivery of the immunogen. Where heptose-1,7-bisphosphate and the immunogen are co-administered, they may be administered in a formulation comprising a simple mixture or the immunogen and heptose-1,7-bisphosphate may physically linked, e.g. by covalent linkage. In this embodiment of the present disclosure, heptose-1,7-bisphosphate may serve as an adjuvant, i.e. a chemical compound that enhances the immune response by stimulation, or additional stimulation, of the immune system, notably when the immunogen used is poorly or not immunogenic when administered alone or when it elicits an immune response that is less desirable than that generated when heptose-1,7-bisphosphate is administered in combination with the immunogen.

The immunogen, in accordance herewith, may be any immunogen, including any antigen against an infectious agent, such as for example an infectious bacterial, viral or parasitic pathogens, including Gram-negative bacterial pathogens belonging to the genus *Neisseria* (including *Neisseria meningitidis, Neisseria gonorrohoeae*), *Escherichia* (including *Escherichia coli*), *Klebsiella* (including *Klebsiella pneumoniae*), *Salmonella* (including *Salmonella typhimurium*), *Shigella* (including *Shigella dysenteriae, Shigella flexneri, Shigella sonnei*), *Vibrio* (including *Vibrio cholerae*), *Helicobacter* (including *Helicobacter pylori*), *Pseudomonas* (including *Pseudomonas aeruginosa*), *Burkholderia* (including *Burkholderia multivorans*), *Haemophilus* (including *Haemophilus influenzae*), *Moraxella* (including *Moraxella catarrhalis*), *Bordetella* (including *Bordetella pertussis*), *Francisella* (including *Francisella tularensis*), *Pasteurella* (including *Pasteurella multocida*), *Legionella* (including *Legionella pneumophila*), *Borrelia* (including *Borrelia burgdorferi*), *Campylobacter* (including *Campylobacter jejuni*), *Yersinia* (including *Yersinia pestis* and *Yersinia enterocolitica*), *Rickettsia* (including *Rickettsia rickettsii*), *Treponema* (including *Treponema pallidum*), *Chlamydia* (including *Chlamydia trachomatis, Chlamydia pneumoniae*) and Brucella spp., and including Gram positive bacterial pathogens belonging to the genus *Staphylococcus* (including *Staphylococcus aureus*), *Streptococcus* (including *Streptococcus pneumoniae, Streptococcus pyogenes*), *Listeria* (including *Listeria monocytogenes*), *Corynebacterium* (including *Corynebacterium diphtheriae*), *Enterococcus* (including *Enterococcus faecalis*), Clostridium spp., and *Mycobacterium* (including *Mycobacterium tuberculosis, Mycobacterium leprae, Mycobacterium avium*).

Immunogens or antigens may also be from pathogenic viruses including Adenoviridae (including Adenovirus), Herpesviridae (including Epstein-Barr virus, Herpes Simplex Viruses, Cytomegalovirus, Varicella Zoster virus), Papillomviridae, Poxviridae (including Papillomavirus), Hepadnaviridae (including Hepatitis B virus), Parvoviridae, Astroviridae, Caliciviridae, Picornaviridae (including Coxsackievirus, Hepatitis A virus, Poliovirus), Coronaviridae, Flaviviridae (including Hepatitis C virus, Dengue virus), Togaviridae (including Rubella virus), Hepeviridae, Retroviridae (including HIV), Orthomyxoviridae (including influenza virus, Arenaviridae, Bunyaviridae, Filoviridae, Paramyxoviridae (including Measles virus, Mumps virus, Parainfluenza virus, Respiratory Syncytial virus), Rhabdoviridae (including Rabies virus) or Reoviridae.

Immunogens or antigens may also be from pathogenic fungal infections including those caused by *Candida, Aspergillus, Cryptococcus, Histoplasma, Pneumocystis,* or *Coccidioides*. Vaccines may also target parasitic pathogens including *Leishmania, Plasmodium, Toxoplasma, Trypanosoma* and *Schistosoma*.

The immunogen or antigen may be from a protein or other antigens expressed on the subject's own cells, such as a tumor antigen or cancer antigen, to stimulate an immune response against the pathogenic cells or tissues. In one embodiment, the HBP may be introduced directly into a tumor to increase the immune response against the tumor.

The immunogen can be administered as part of a vaccine formulation.

Compositions

The present disclosure further provides a pharmaceutical composition for modulating an immune response comprising an effective amount of a TIFA activator such as heptose-1,7-bisphosphate. In one embodiment, such compositions are for enhancing an immune response. In another embodiment, such compositions are for modulating an inflammatory response. In another embodiment such compositions are for preventing, treating, ameliorating, or inhibiting an injury, disease, disorder or condition.

The pharmaceutical preparation in accordance herewith in addition to a TIFA activator such as heptose-1,7-bisphosphate, may optionally contain additional ingredients, including a carrier. Such ingredients are primarily determined by the mode in which the preparation is delivered. Thus a composition that is delivered orally in tablet form, may include, in addition to heptose-1,7-bisphosphate, a biologically acceptable carrier, a filler (e.g. lactose), a binder (e.g. cellulose, gelatin, gum arabic), an (additional) adjuvant, a flavoring agent, a coloring agent, a coating material (e.g. a wax or plasticizer), and the like. A preparation to be delivered in liquid form may additionally contain e.g. a biologically acceptable carrier, a diluent, an emulsifying agent, coloring agent, and/or a flavoring agent. A composition for parenteral administration, may be mixed and dissolved in a diluent such as water, sterile saline, PBS, or other biologically acceptable carrier. The form in which the pharmaceutical preparation is administered (e.g. tablet, powder, emulsion, solution, capsule) depends on the mode of delivery. As hereinbefore noted the quantity of heptose-1,7-bisphosphate in a single pharmaceutical dose may vary and typically depends on a variety of factors such as, the injury, disease, disorder indication or condition, the route or mode of administration, the administration regimen, the severity of the condition, the subject's general health, age, and weight, and dosage of the formulation, and other factors. A single dose ranges typically between approximately 0.001 mg and 500.00 mg of heptose-1,7-bisphosphate per kilogram of body weight. In general, a person of skill in the art will be able to readily determine the effective amount constituting a single dose.

In one embodiment, the pharmaceutical compositions may additionally include an immunogen or antigen as hereinbefore described. The immunogen or antigen may be in a vaccine formulation.

Stimulating Molecular Receptor

The present disclosure further provides a method for stimulating a molecular receptor of heptose-1,7-bisphosphate capable of molecular signaling upon contact with heptose-1,7-bisphosphate. In accordance herewith heptose-1,7-bisphosphate may be used to stimulate a molecular receptor. The performance of such stimulation may be conducted in vitro or in vivo, by providing heptose-1,7-bisphosphate, more or less pure form, and contacting it with the molecular receptor, such receptor preferably being expressed by a primary or immortalized cell. In preferred embodiments, this will lead to the activation of the human protein TRAF-interacting forkhead-associated protein A ("TIFA"), encoded by a human polynucleotide (see: SEQ.ID.NO: 1) encoding the TIFA polypeptide (see: SEQ.ID.NO: 2). The TIFA polypeptide may be purified from human cells or produced recombinantly in e.g. bacterial cells or human cells, using, for example the polynucleotide sequence set forth in SEQ.ID.NO: 1, linked to polynucleotides capable of regulating expression in a cell, such as a promoter, thus creating chimeric polynucleotides comprising a polynucleotide encoding a TIFA polypeptide. In in vivo embodiments, additional constituents may be present, notably other molecular compounds that interact with TIFA in a manner dependent on the presence of heptose-1,7-bisphosphate, such as the ubiquitin ligase TRAF6. The effect of over-expressing TIFA polypeptide in cell lines, which leads to constitutive binding of TIFA to the TRAF proteins TRAF6 and/or TRAF2 and, ultimately, to the activation of the transcription factor NF-κB, has been described (WO2002057449A1, WO2003082917A1). However, no agonists have been described that activate TIFA in a physiological relevant setting, and no role for TIFA in a physiologically relevant cell response have been previously described.

Screening Methods

The present disclosure still further provides methods for selecting a compound capable of modulating an immune response in a subject in need thereof by effecting a TIFA signaling response, the method comprising:

(a) providing a test compound with the potential to effect TIFA in a manner that results in a TIFA signaling response;

(b) comparing in a functional assay the effect of the test compound on TIFA with a control; and (c) selecting a test compound exhibiting an effect on the signaling response of TIFA for further evaluation.

In certain embodiments, the compound is a polynucleotide. In certain embodiments the control comprises performance of the functional assay using a cell that does not express TIFA as a negative control. In other embodiments, the control comprises HBP as a positive control.

In accordance with the foregoing, a test compound may be evaluated for its potential to result in a TIFA signaling response. The test compound may be any compound, including a polynucleotide, capable of effecting a TIFA signaling response, including any signaling response resulting from direct interaction of the compound with TIFA, or indirect interaction of the compound with TIFA, for example, interaction of the chemical with a cellular constituent which upon such interaction, directly or indirectly, interacts with TIFA in a manner that results in a TIFA signaling response. Thus for example, a chemical compound may interact with a kinase which phosphorylates TIFA, resulting in a TIFA signaling response. The signaling response may be an activation or an inhibition of TIFA activity. Typically this is achieved by providing one or a more compounds that one wishes to test and the performance of a functional assay. The assay is preferably an in vitro assay, and may be configured so that multiple compounds can be evaluated simultaneously. The functional assay may be any assay that is capable of detecting a TIFA signaling response. For example, the assay may involve evaluation of an effect of the compound on TRAF6 and/or NF-κB, notably in the presence of a negative control (e.g. an innocuous compound, or an innocuous bacterial strain, including for example, a *Neisseria* strain in which the gmhA or hldA genes had been inactivated) and/or a positive control, such as heptose-1,7-bisphosphate. Furthermore cells lacking TIFA in these assays could be used to confirm that the observed effects are dependent on TIFA signaling. Thus in preferred embodiments, comparing in a functional assay the effect of the test compound on TIFA with a control comprises evaluating the effect of the test compound on cells expressing TIFA and evaluating the effect of the test compound on cells expressing versus cells not expressing TIFA.

Upon selecting a compound exhibiting an effect on a TIFA signaling response, the compound is selected for further evaluation, which may include testing of the compound in in vitro or in vivo tests for TIFA signaling response or in other manners. For example, in vitro tests may include monitoring the phosphorylation of TIFA, using polyacrylamide gel electrophoresis (PAGE) in native conditions to monitor the oligomerization status of TIFA following treatment with the compound, co-immunoprecipitation of TIFA with downstream effector TRAF6, or the assembly of TIFA into large structures evident by immunofluorescence microscopy. Furthermore, the effect of compounds that mediate their effects via TIFA can also be tested in animal models, preferably by comparing the effect in animals that either do or do not express TIFA. Testing may also include administration of the chemical compound to a human.

EXAMPLES

Example 1—Preparing Heptose-1,7-Bisphosphate

*N. meningitis* gmhA and hldA genes were amplified and cloned into pET28a (Novagen). *E. coli* BL21(DE3) were transformed, selected with 50 μg/ml kanamycin, and starter cultures grown to an $OD_{600}$=0.6 Cultures were induced with 0.5 mM IPTG for 4 hr and harvested by centrifugation. Pellets were re-suspended in lysis buffer: 50 mM TRIS pH 8.0, 300 mM NaCl, 10 mM imidazole, 3 mM 2-Mercaptoethanol. Clarified lysates were prepared by sonication followed by centrifugation at 20,000×g for 30 min. Proteins were purified with Ni-NTA agarose (Qiagen) using Amicon® Pro purification system with 10 kDa cut-off (Millipore). Proteins were eluted in lysis buffer containing 300 mM imidazole and buffer exchange was done using 50 mM HEPES pH 8.0, 100 mM KCl, 1 mM DTT. Enzymes were stored in 50% glycerol. HBP was enzymatically synthesized in the following reaction: 20 mM HEPES pH 8.0, 20 mM KCl, 10 mM $MgCl_2$, 10 mM sedoheptulose 7-phosphate (Sigma), 20 mM ATP, 5 µg GmhA, and 3 µg HldA. Reactions were stopped by incubating at 95° C. for 5 min, and then passed through a 0.22 µm filter.

Example 2—Stimulation of the Immune System by Heptose-1,7-Bisphosphate

*Neisseria* spp. secrete a metabolite that activates NF-κB in 293 and Jurkat T cell lines; cell types whose ability to respond to previously-described PAMPs is limited to TLR5-dependent detection of flagellin (Malott et al., 2013). While the neisserial gene hldA is essential for this process, the identity of the molecule remains unknown. HldA catalyzes the second step in the synthesis of ADP-heptose (ADP-hep), the precursor for the inner core region of LPS (or lipooligosaccharide (LOS) in *Neisseria* spp.), the major component of the Gram-negative outer membrane (Kneidinger et al., 2002) (FIG. 1a). To identify the molecule, we sought the first step in the ADP-hep biosynthetic pathway downstream of HldA that was dispensable for culture supernatant-mediated NF-κB activation. Supernatant from the *N. meningitis* ΔgmhB mutant, whose terminal metabolite in the ADP-hep pathway differs from the ΔhldA mutant by a single phosphate group, potently activates NF-κB (FIG. 1b). Thus, by permitting the synthesis of D-glycerol-D-manno-heptose-1,7-bisphosphate (HBP), we restored the pro-inflammatory nature of *Neisseria* culture supernatants. The ΔgmhB and ΔhldA *N. meningitis* mutants both display the so-called "deep-rough" phenotype (Schnaitman and Klena, 1993) possessing heptoseless LOS truncated after the Kdo sugars (FIG. 1c) indicating that HBP elicits an inflammatory response regardless of whether heptose is incorporated into the LOS. Next, we enzymatically synthesized HBP from sedoheptulose-7 phosphate (S7P) using GmhA and HldA purified from *N. meningitis*. The product of the in vitro reaction potently stimulated NF-κB only when the substrate and both enzymes were supplied (FIG. 1d). Furthermore, incubation of the product with the downstream phosphatase GmhB decreased NF-κB activation (FIG. 1e). Thus, HBP is the innate immune agonist shed by *Neisseria*.

Figure 2:
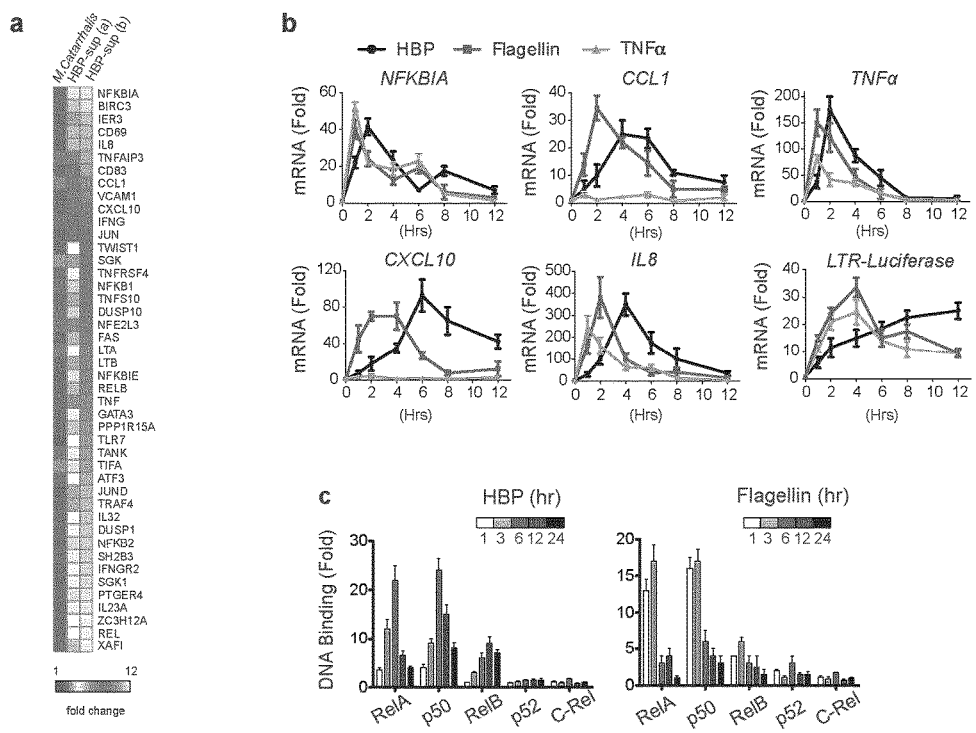
FIG. 2. Shown in FIG. 2(a) is a micro array analysis of Jurkat T cells treated with purified culture supernatants prepared from *N. gonorrhoeae* or *M. catarrhalis* for 2 hrs. Shown is the mean fold change of unregulated genes (>1.5 fold) from two clonal populations (a,b) compared to *M. catarrhalis* done in technical triplicate. The first column depicts the fold difference between the baseline expression values of clone a and b when treated with *M. catarrhalis* supernatant.
Figure 3:
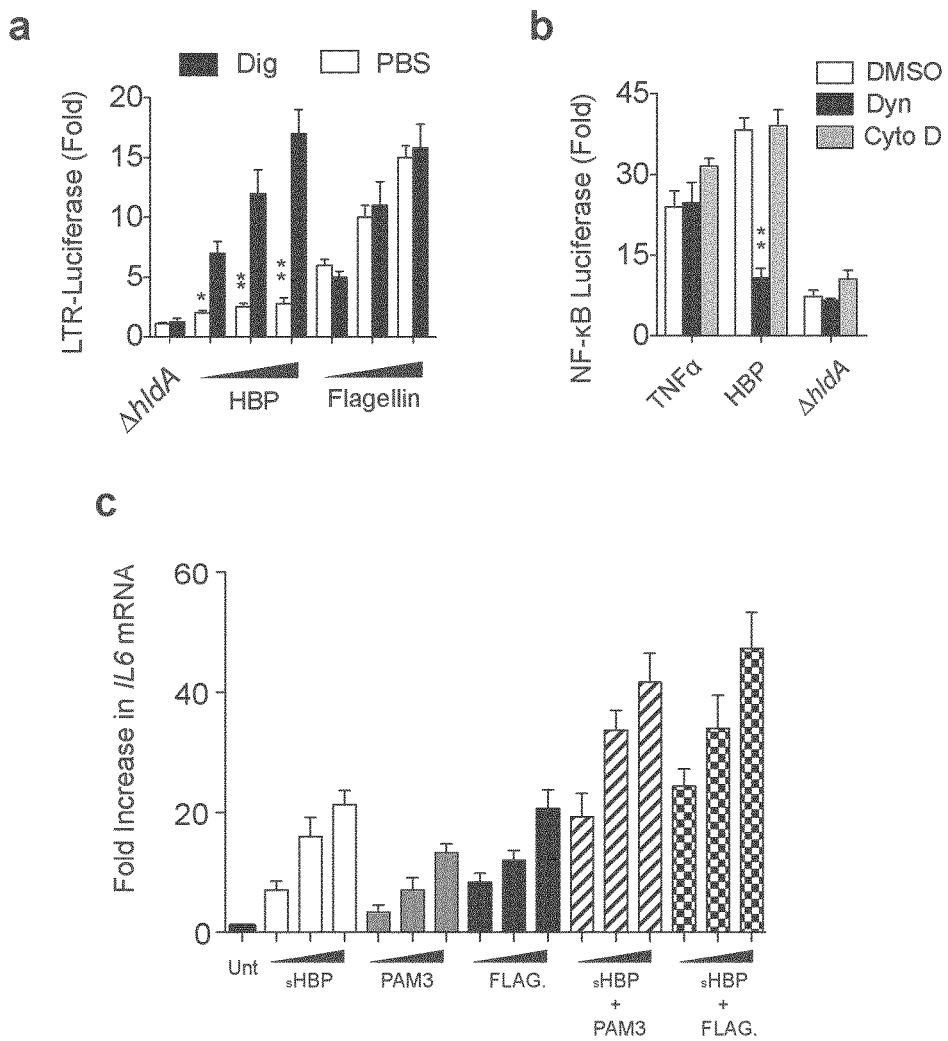
FIG. 3. Shown in FIG. 3(a) are Jurkat 1G5 cells, stably expressing a HIV long terminal repeat (LTR)-driven luciferase, treated with increasing amounts of HBP containing or deficient (ΔhldA) supernatants, or flagellin in the presence or absence of digitonin (Dig) for 15 minutes. Media was replaced and luciferase activity determined after 6 hrs.

HBP-containing supernatants up-regulated a variety of NF-κB dependent genes in Jurkat T cells (FIG. 2a). Interestingly, the kinetics of HBP-mediated NF-κB activation and resulting pro-inflammatory transcriptional response was slower, and persisted longer, than stimulation with flagellin or TNFα, two ligands that signal at the cell surface (FIG. 2b,c). Therefore, we hypothesized that HBP first required entry into the host cytosol to signal. Indeed, delivery of HBP-containing supernatants into the cytosol of Jurkat 1G5 cells, which harbor a stable HIV LTR-luciferase construct (Aguilar-Cordova et al., 1994), using reversible digitonin permeabilization (Girardin et al., 2003) resulted in a dose-dependent increase in luciferase activity, whereas TLR5-mediated activation remained constant (FIG. 3a). Like other cytosolic PAMPs, synthetic HBP synergistically activated THP-1 macrophages in combination with TLR ligands (FIG. 3c). To determine how HBP gains entry to the cytosol we treated 293T cells with a highly specific inhibitor of the GTPase dynamin (dynasore) (Macia et al., 2006), or cytochalasin D, an inhibitor of actin polymerization. Dynasore, but not cytochalasin D, attenuated the NF-κB response to HBP (FIG. 3b). Thus, HBP signals in the host cytosol following internalization via dynamin-dependent endocytosis.

Figure 4:
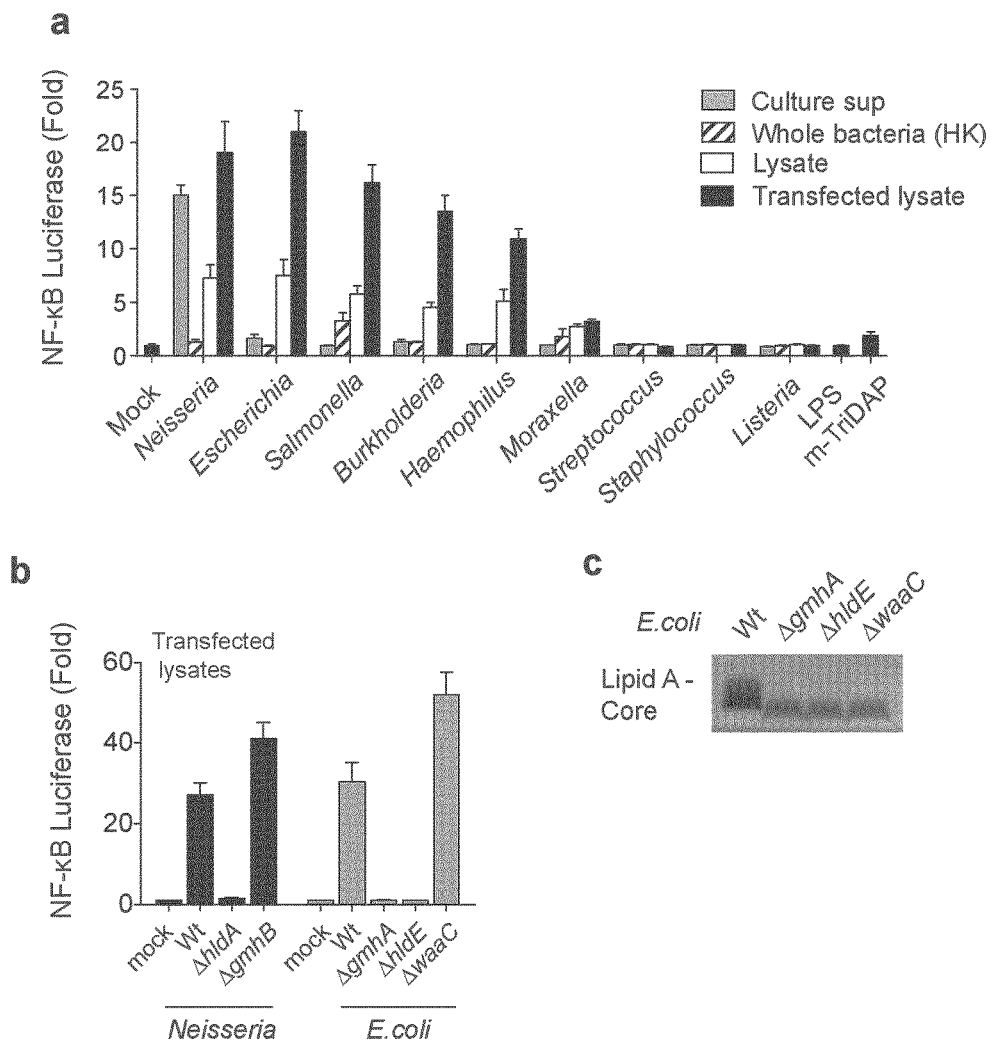
FIG. 4. Shown in FIG. 4(a) is NF-κB luciferase activity in 293T cells treated for 6 hr with culture supernatant, heat-killed (HK) whole bacteria, soluble lysate, or transfected with soluble lysate prepared from Gram-negative or Gram-positive bacteria.
Figure 5:
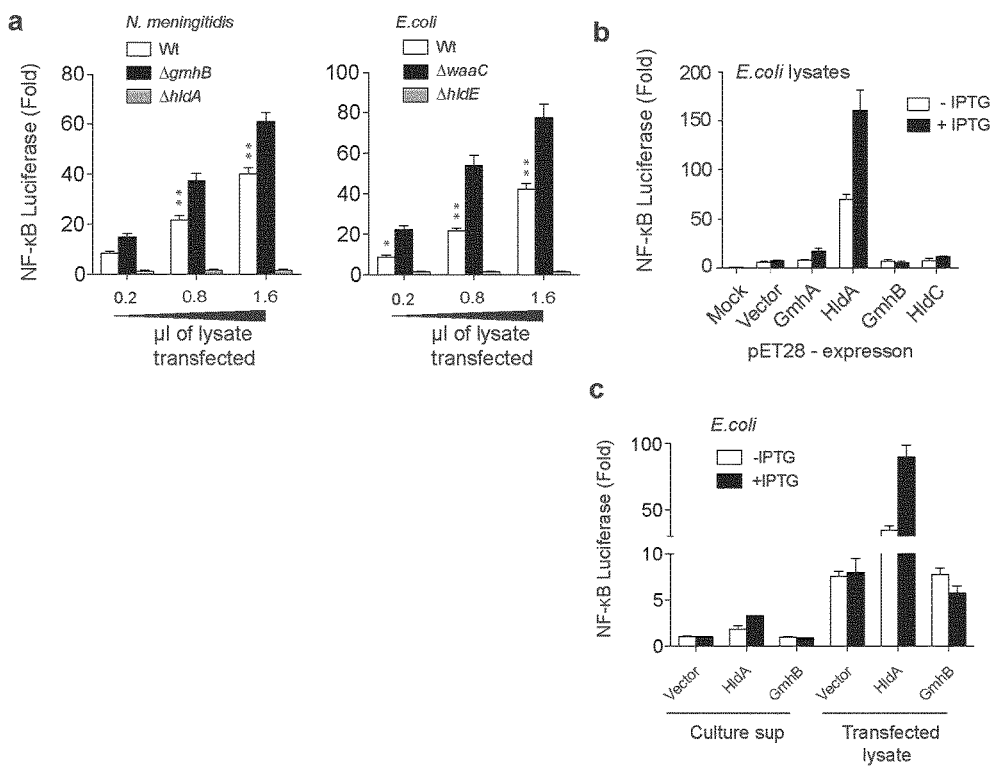
FIG. 5. Shown in FIG. 5(a) is, NF-κB luciferase activity of 293T cells transfected with the indicated volume of soluble lysates form wild-type (Wt) or mutants lacking genes upstream of HBP (ΔhldA or ΔhldE), or downstream of HBP (ΔgmhB, or ΔwaaC) in the ADP-Hep pathway in *N. meningitis* or *E. coli*.

HBP is an intermediate in a biosynthetic pathway conserved in most Gram-negative bacteria (Kneidinger et al., 2002). However, being a cytosolic bacterial metabolite that must enter the host cell to signal, we hypothesized HBP-mediated signaling by other, non-*Neisseria*, Gram-negative bacteria would require its liberation from inside the bacterial cytosol. To test this in non-phagocytic cells, we transfected soluble lysates from a variety of bacterial Genera into 293T cells containing an NE-κB reporter. Transfection of Gram-negative lysates, with the notable exception of *Moraxella*, potently activated NF-κB, while Gram-positive lysates had no activity (FIG. 4a). Importantly, *Moraxella* is one of the few Gram-negative bacteria that lack the ADP-hep pathway (Caroff and Karibian, 2003). NF-κB activation depended on the release of bacterial cytosolic components, as heat-killed whole bacteria showed no activity. Cells were unresponsive to the two known PAMPs unique to Gram-negative bacteria, LPS and the NOD1 ligand m-TriDAP, suggesting that a novel PAMP was responsible for activating NF-κB. Remarkably, deletion of genes upstream of HBP in the ADP-hep pathway in either *N. meningitis* or *E. coli*, completely abrogated lysate-mediated NF-κB activation (FIG. 4b). Mutants lacking genes in the pathway downstream of the HBP intermediate, waaC (rfaC) in *E. coli*, or gmhB in *N. meningitis*, potently activate NF-κB (FIG. 4b,c). In fact, deletion of either gene significantly increased NF-κB activation, implicating an intracellular buildup of HBP (FIG. 5a). Importantly, the HBP-effect could be exacerbated in wild type *E. coli*, as over-expression of *Neisseria* HldA, but not other enzymes in the ADP-hep pathway in wild type *E. coli* (BL21) increased lysate-mediated NF-κB activation over 100-fold (FIG. 5b). Interestingly, HBP did not accumulate in the culture supernatant in the HldA—over expressing *E. coli*, suggesting a unique mechanism for HBP release exists in *Neisseria* spp.

Figure 6:
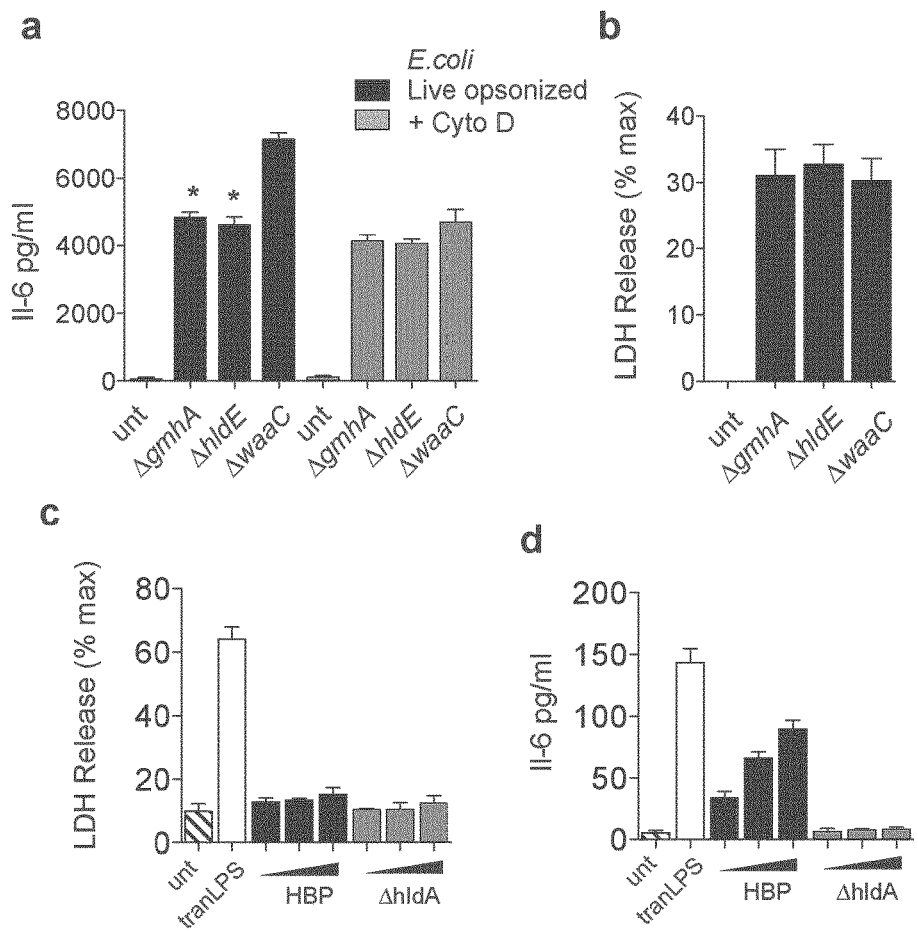
FIG. 6. Shown are IL-6 levels (20 hr) (FIG. 6(a)), or pyroptosis by LDH release (20 hr) (FIG. 6(b)) after infection of THP-1 macrophages with serum-opsonized *E. coli* of the indicated genotype with or without pre-treatment with cytochalasin D. THP-1 macrophages treated with HBP-containing or deficient supernatants or transfected with LPS form *E. coli* for 6 hr and IL-6 production (FIG. 6(c)), or pyroptosis by LDH release (FIG. 6(d)) determined. Data represent ≥3 independent experiments performed in duplicate. All error bars±s.e.m.

A PAMP only accessible to host cells following bacterial lysis, we hypothesized that the primary method of HBP liberation in vivo would be through phagocytosis. Indeed, infection of THP-1 macrophages with serum-opsonized HBP-synthesizing *E. coli* (ΔwaaC) induced more IL-6 production, but not more pyroptotic cell death, than HBP-lacking *E. coli* of the same LPS phenotype (ΔhldE, ΔgmhA) (FIG. 6a,b). Importantly, pre-treatment with cytochalasin D abrogated the effect. HBP containing supernatants also did not induce pyroptosis in THP-1 differentiated macrophages, despite inducing significant IL-6 production (FIG. 6c,d). Given that HBP is only liberated from non-*Neisseria* following bacterial degradation, the lack of a self-destructive inflammatory cell death response to HBP likely allows the cell to detect degraded bacterial products in the cytosol without undergoing the danger-associated pyroptosis. Thus, there is immunoactive HBP in the cytoplasm of many Gram-negative bacteria that is liberated during lysis or phagocytosis, activating NF-κB without triggering cell death.

293 cells have previously been reported to express endogenous levels of NOD1 and NOD2 (Girardin et al., 2003).

Figure 7:
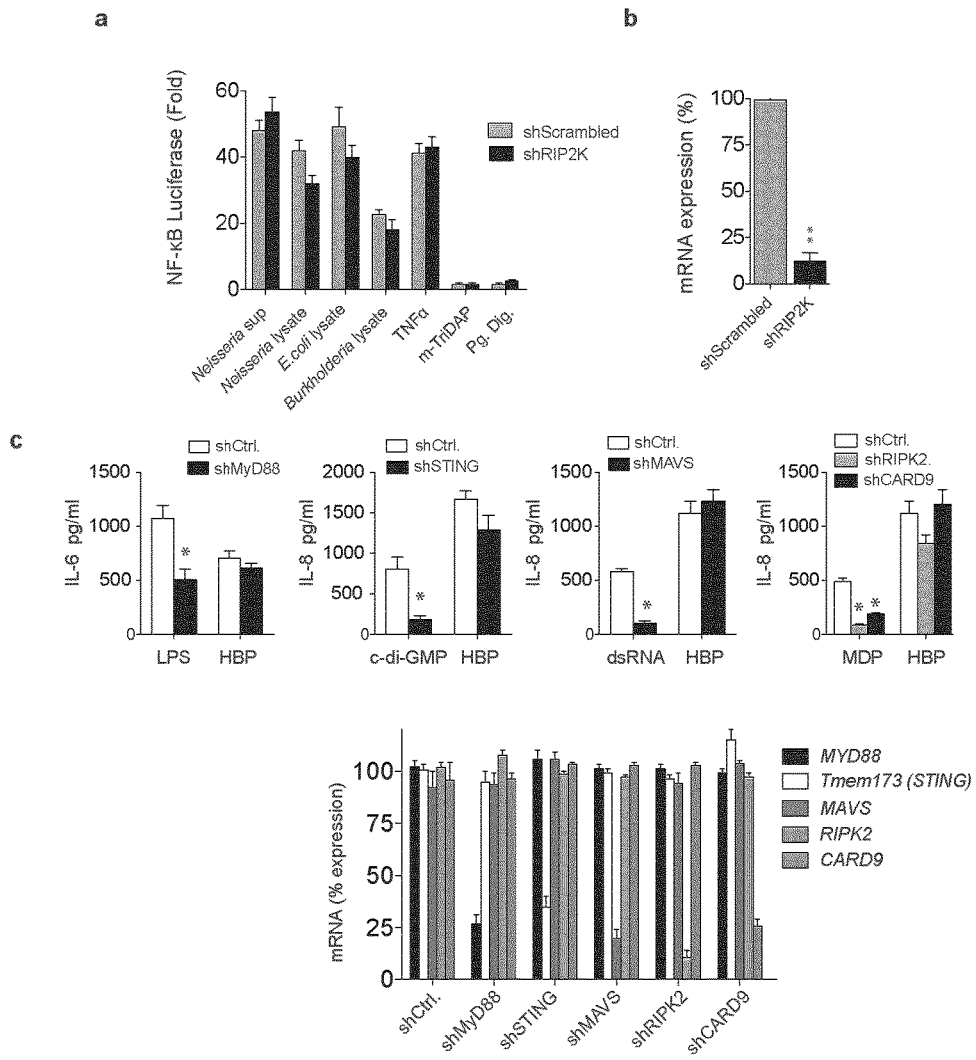
FIG. 7. Shown in FIG. 7 (a) is NF-κB luciferase activity following RIP2 knockdown in 293T treated with HBP, the NOD1 ligand mTri-DAP, purified and mutanolysin digested peptidoglycan (Pg. Dig.) from *N. gonorrhoeae*, TNFα, or transfected with lysates from the indicated bacteria.

HBP signaling was independent of NOD1/2, as shRNA knockdown of RIP2, which is essential for NOD1/2 signaling (Kobayashi et al., 2002), had no significant effect on HBP or lysate-mediated NF-κB activation (FIG. 7a,b). Moreover, shRNA knockdown of the adaptor proteins MyD88, RIP2, CARD9, STING, and MAVS, which mediate signaling from other known cellular pattern recognition receptors (Medzhitov et al., 1998), (Hara et al., 2007), (Parvatiyar et al., 2012), (Meylan et al., 2005), (Kawai et al., 2005), (Seth et al., 2005), had no significant effect on HBP-mediated cytokine production in THP-1 macrophages (FIG. 7c, 8e) suggesting HBP is detected by a previously undescribed pathway.

Figure 8:
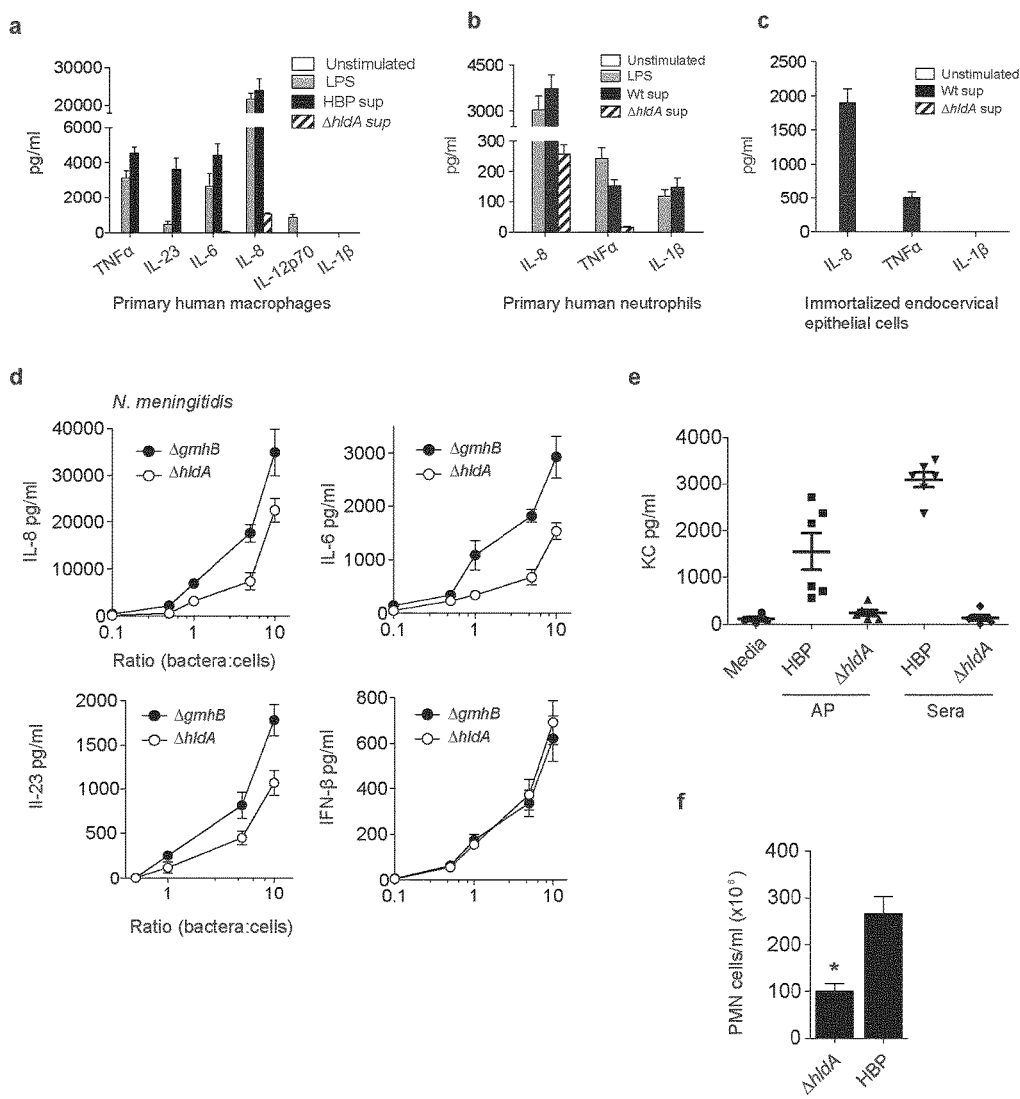
FIG. 8. Shown is Cytokine production following treatment of primary human macrophages (FIG. 8 (a)) primary human neutrophils (FIG. 8 (b)) or immortalized epithelial cells from the human endocervix (FIG. 8 (c)) with purified HBP containing (Wt) or deficient (ΔhldA) supernatants from *N. gonorrhoeae* or LPS (24 hr).
Figure 9:
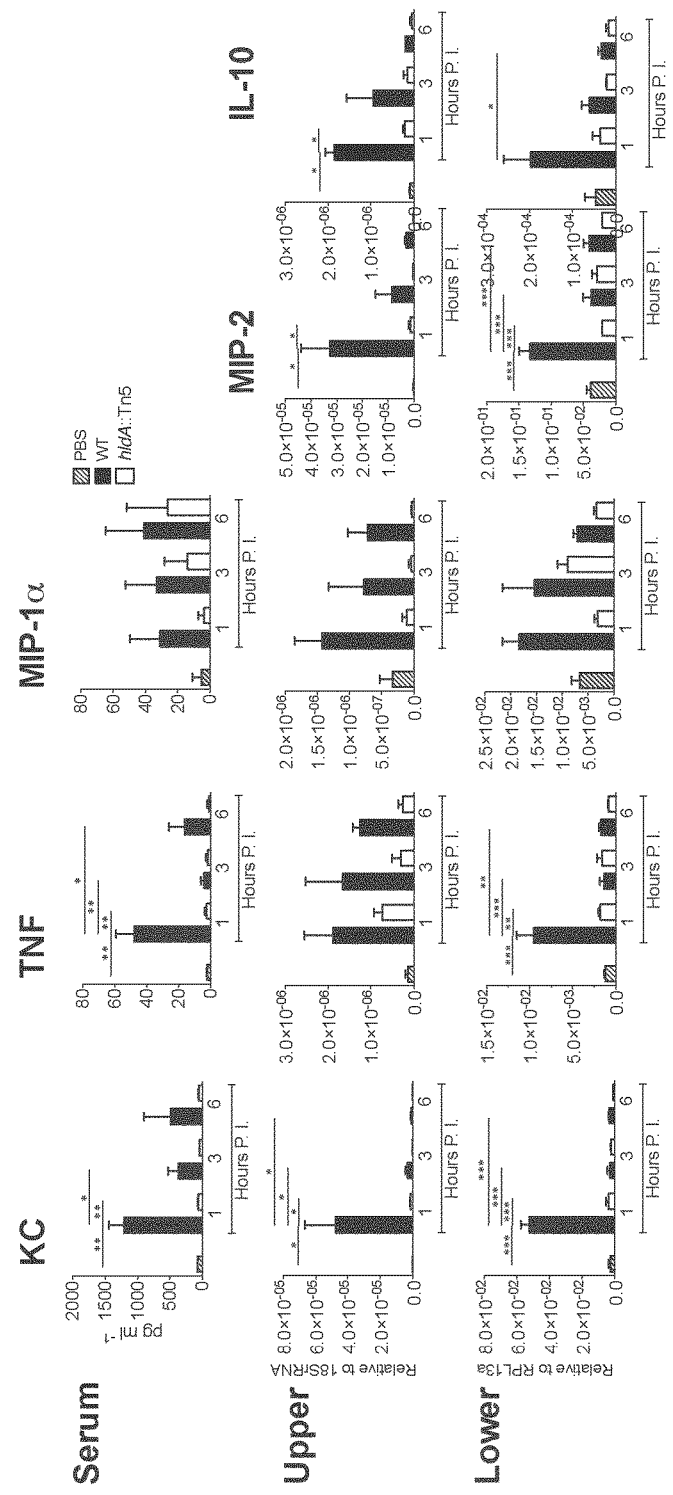
FIG. 9. Shown is intrauterine HBP induces local and systemic inflammation in mice at diestrus. Expression of cytokines in wild type (WT) mice at diestrus (naturally cycling) post-transcervical inoculation (P.I.) with PBS (hatched bars), preps from WT gonococci (WT, black bars), or preps from hldA:Tn5 gonococci (ΔHBP, white bars). Mice were sacrificed at 1, 3, or 6 hours P.I. Relative expression of proinflammatory cytokines (KC, TNF, MIP-1α, MIP-2) and anti-inflammatory cytokine IL-10 in the upper and lower genital tract were analyzed by qRT-PCR. Serum expression of general proinflammatory cytokines were analyzed by ELISA. n=2-4 per group. Data shown are means±SEM. *p<0.05, p<0.01, *p<0.01; one-way ANOVA; Tukey.
Figure 10:
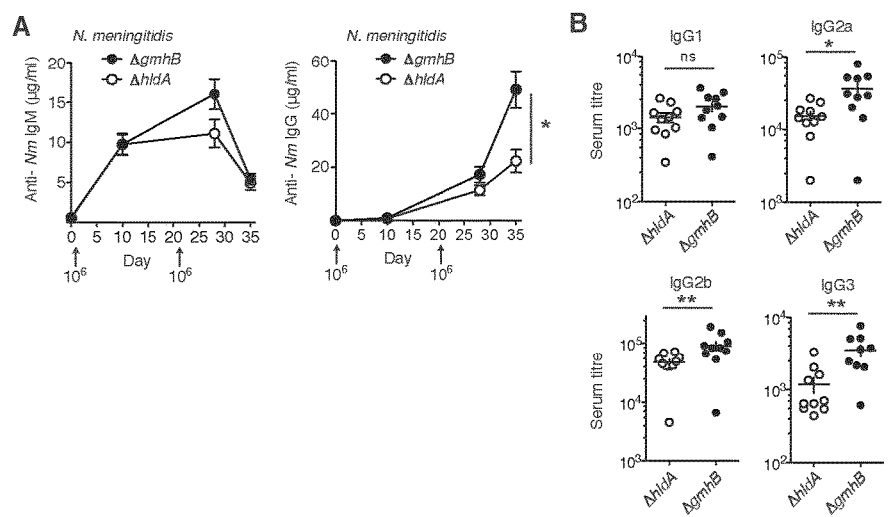
FIG. 10. Shown in FIG. 10 (A) is total anti-*N. meningitidis* (Nm) IgM or IgG serum titres at the indicated day, or individual IgG subclasses at day 35 FIG. 10 (B) by whole bacteria ELISA following immunization and rechallenge of mice with 1×10$^6$ live *N. meningitidis* of the indicated genotype (n=10). Bacteria were cleared within <12 h of injection. *P<0.05, P<0.01, *P<0.001 by ANOVA (A, C) or by t-test (B, D). ns, not statistically significant.

In primary cells, HBP induced IL-8, IL-6, and TNFα production in differentiated primary human macrophages, neutrophils, and immortalized epithelial cells (FIG. 8a-c) and infection of macrophages with N. meningitidis ΔgmhB induced more IL-6, IL-8, and IL-23, but not IFN-β than the ΔhldA mutant, which differs only in its ability to synthesize HBP. Notably, HBP induced significant amounts of the Th17 polarizing cytokines IL-6 and IL-23. To assess the activity of HBP in vivo, we used the mouse air pouch as a model to study acute inflammation in a sterile tissue (Edwards et al., 1981). Injection of HBP-containing supernatants absent microbial product contamination into the sterile compartment induced a local and systemic inflammatory response, evidenced by an increase in local and systemic accumulation of the neutrophil-targeting keratinocyte derived chemokine (KC), and culminating in a 3-fold increase in neutrophil recruitment to the air pouch (FIG. 8e,f). Moreover, injection of HBP-containing supernatants purified from N. gonorrhoeae into the genital tract of mice induced local and systemic cytokine production in from 1 to 6 h post inoculation (FIG. 9). Therefore, similar to NOD1-mediated recruitment of neutrophils (Masumoto et al., 2006), HBP in the host cytosol is an alarm signal that stimulates innate cytokine production and recruits neutrophils to the site of infection. Innate recognition of PAMPs provides critical instruction to the onset of adaptive immunity (Iwasaki and Medzhitov, 2010). The ability of PAMPs to modulate immune cell maturation, cytokine production, and antigen presentation offers exciting potential for their use as vaccine adjuvants and cancer immunotherapy (Carter and Reed, 2010; Maisonneuve et al., 2014; Deng et al., 2014; Adams 2009). Therefore, we analyzed the antibody titers produced following immunization of mice with N. meningitidis ΔgmhB or ΔhldA, strains that differ only the presence of HBP. The HBP-producing strain (ΔgmhB) induced a transient increase in meningococcal-specific IgM, and significantly more class-switched anti-meningococcal IgG, in particular Th1-associated subclasses IgG2a, b and IgG3, upon rechallenge (FIG. 10). This indicated that HBP can prime adaptive immune responses in vivo, speaking to its potential as a vaccine adjuvant.

We have demonstrated that HBP is a novel PAMP, unique to Gram-negative bacteria, that triggers NF-κB activation upon entry into the host cytosol. Detection of HBP lacks the aggressive inflammatory characteristics associated with the detection of cytosolic LPS (Hagar et al., 2013), (Kayagaki et al., 2013), flagellin (Franchi et al., 2006), or prokaryotic RNA (Sander et al., 2011) that signify intracellular invasion. Given that HBP does not require invasion to access the cytosol, the detection of HBP likely allows our innate immune system to detect phagosome-degraded bacterial components in the cytosol at lower threat level and with differing kinetics than surface TLRs, alerting the immune response to bacteria without the need to trigger associated inflammatory cell death.

Methods

Cell Culture, Luciferase Assays 293T were maintained in DMEM supplemented with 10% FBS, 1% glutamax, and 1% penicillin streptomycin. Jurkat 1G5 cells contain a stably-integrated LTR-luciferase reporter gene (Aguilar-Cordova et al., 1994), and were maintained in RPMI supplemented with 10% FBS and 1% glutamax. THP-1 cells were maintained in RPMI supplemented with 10% FBS and 1% glutamax and differentiated to macrophages with 50 ng/ml PMA for 48 hr, followed by a 48 hr rest period prior to stimulation. To measure LTR-driven luciferase, 1G5 cells were lysed and luminescence determined using the Luciferase Assay kit (Promega) according to manufacturer's instructions. Results are expressed as fold change compared to untreated. 293T cells were transfected in 96 well plates with 90 ng ELAM firefly luciferase reporter plasmid (Chow et al., 1999) and 10 ng pRL-TK Renilla plasmid using TransiT LTI (Mirus). 18 hours later cells were treated for 6 hours and luciferase activity determined using the Dual-Glo Luciferase Assay System (Promega). Results are expressed as fold increase relative to transfected, mock treated cells following normalization to Renilla luciferase. Digitonin permeabilization assays were done as described previously (Girardin et al., 2003) with the following modifications: 1G5 cells were stimulated with purified HBP supernatants, or 10 μg/ml flagellin (Invivogen) for 20 minutes at 4° C. in the absence or presence of 2 μg/ml digitonin (Sigma). To assess HBP internalization, 293T were transfected as above, then treated with 80 μM Dynasore (Sigma), or 10 μM cytochalasin D for 1 hr prior to stimulation with purified HBP, 20 ng/ml TNFα, or ΔhldA-HBP.

Bacteria

Bacterial strains used were the following: N. gonorrhoeae MS11 (Opa⁻, pilus⁻), ΔhldA: Tn5 N. gonorrhoeae MS11 (Opa⁻, pilus⁻) (Malott et al., 2013), N. meningitis B16B6, N. meningitis B16B6 ΔhldA:Tn5 (Malott et al., 2013), E. coli DH5α, E. coli BL21 (DE3), S. typhimurium strain 14028S, B. multivorans pulmonary isolate from CF patient, H. influenzae 1128 middle ear isolate, S. pneumoniae sputum isolate, S. aureus ATCC 29213 skin wound isolate, and L. monocytogenes EGD-e. To generate N. meningitis mutants, overnight cultures of N. meningitis B16B6 were spot transformed with 10 μg pUC19 containing a KAN-2 kanamycin cassette (Epicentre) flanked by ±500 bp flanking regions of gmhB, or hldD. pUC19 Targeting vector:

gmhB (SEQ ID NO: 7)
5'-agctcggtacccggggatcctctagagaagttacaatgagc
ccttttagagg-3'
and (SEQ ID NO: 8)
5'-acagctatgaccatgattacgccaagctttccgggcgcaaggcgcgtg
cctcc-3';

hldD ((SEQ ID NO: 9)
5'-agctcggtacccggggatcctctagaagaaataccggcttca
gaatttaatc-3'
and

```
                                                (SEQ ID NO: 10)
5'-acagctatgaccatgattacgccaagcttaccgggctacgtcggctttg
aac-3.

KAN-2 cassette amplification: gmhB
                                                (SEQ ID NO: 11)
5'-gaacctgcccaaaccaaaggaaacgcgcaaccatcatcgatgaattgt
g-3
and (SEQ ID NO: 12)
5'-tttgccttgtcggaaatgcggtatgtcaaccctgaagcttgcatg-3' hIdD
                                                (SEQ ID NO: 13)
5'-ttttactcaaaacaaaggaaaccgaatcaaccatcatcgatgaattgt
g-3'
and (SEQ ID NO: 14)
5'-ttctttcaaacaaaattaccaatcgtgtcaaccctgaagcttgcat
g-3'.
```

Restriction-free cloning was used to replace the gmhB, and hldD open reading frames in pUC19 with the amplified KAN-2 cassettes (van den Ent and Löwe, 2006). Following transformation and selection using 80 µg/ml kanamycin, genotyping was done with the following primers:

```
gmhB
                                                (SEQ ID NO: 15)
5'-acctgcccaaaccaaaggaaacg-3'
and
                                                (SEQ ID NO: 16)
5'-atggttttgccttgtggaaatgc-3;

hIdD
                                                (SEQ ID NO: 17)
5'-aacatcgtcaaagcacttaatcaacgc-3'
and
                                                (SEQ ID NO: 18)
5'-cgtgttgtccgtaaacgttgaagtag-3'.
```

In E. coli DH5α, gmhA, hIdE, and waaC genes were deleted using the λ-Red plasmid pTP233 (Poteete and Fenton, 1984). Log phase bacteria were induced for 4 hours with 0.5 mM IPTG in the presence of 25 µg/ml tetracycline, washed 3 times with cold 10% glycerol and transformed via electroporation with the gel-purified Kan cassette. Kanamycin cassettes flanked by homology arms were generated by PCR using the following primers:

```
gmhA
                                                (SEQ ID NO: 19)
5'-ctgcattttgtctattacatttatgctgaaggatatcctcgtgtaggc
tggagctgcttc-3'
and
                                                (SEQ ID NO: 20)
5'-ccggatgcggcgtaaacgtcttatccggcctacgccagaccatatgaa
tatcctccttag-3';

hidE
                                                (SEQ ID NO: 21)
5-tattatcgcgcgcaaatttgaatctctcaggagacaggagtgtaggct
ggagctgcttc-3'
and (SEQ ID NO: 22)
5'-cctgccatgtacgaagcgagatctgtgaaccgctttccggcatatgaa
tatcctccttag-3';

waaC
                                                (SEQ ID NO: 23)
5'-agaactcaacgcgctattgttacaagaggaagcctgacgggtgtaggc
tggagctgcttc-3'
and (SEQ ID NO: 24)
5'-tcaatgaatgaagtttaaaggatgttagcatgttttacctcatatgaa
tatcctccttag-3'.
```

Following selection with 50 µg/ml kanamycin, genotyping was done by colony PCR using the following primers:

```
gmhA
                                                (SEQ ID NO: 25)
5'-tagcacctgcccgtacttctcgc-3'
and
                                                (SEQ ID NO: 26)
5'-agacgcgtcagcgtcgcatdagg-3';

hIdE
                                                (SEQ ID NO: 27)
5'-aggtgttgatccgcagccgctgc-3'
and
                                                (SEQ ID NO: 28)
5'-acgacactacccagtcgaccgc-3';

waaC
                                                (SEQ ID NO: 29)
5'-gctgccgttgagcgagttattcctg-3'
and
                                                (SEQ ID NO: 30)
5'-cttccgccagtcgtttcgcccg-3'.
```

LPS and LOS Preparations were prepared from proteinase K-treated cell lysates and visualized by silver staining (Hitchcock and Brown, 1983).

Protein Purification and Heptose 1,7-Bisphosphate (HBP) Synthesis

N. meningitis gmhA, hldA, and gmhB genes were amplified and cloned into pET28a (Novagen). E. coli BL21(DE3) were transformed, selected with 50 µg/ml kanamycin, and starter cultures grown to an $OD_{600}$=0.6. Cultures were induced with 0.5 mM IPTG for 4 hr and harvested by centrifugation. Pellets were re-suspended in lysis buffer: 50 mM TRIS pH 8.0, 300 mM NaCl, 10 mM imidazole, 3 mM 2-Mercaptoethanol. Clarified lysates were prepared by sonication followed by centrifugation at 20,000×g for 30 min. Proteins were purified with Ni-NTA agarose (Qiagen) using Amicon® Pro purification system with 10 kDa cut-off (Millipore). Proteins were eluted in lysis buffer containing 300 mM imidazole and buffer exchange was done using 50 mM HEPES pH 8.0, 100 mM KCl, 1 mM DTT. Enzymes were stored in 50% glycerol. HBP was enzymatically synthesized in the following reaction: 20 mM HEPES pH 8.0, 20 mM KCl, 10 mM $MgCl_2$ 10 mM sedoheptulose 7-phosphate (Sigma), 20 mM ATP, 5 µg GmhA, and 3 µg HldA. Reactions were stopped by incubating at 95° C. for 5 min, and then passed through a 0.22 µm filter. Where indicated, filtrate was then incubated with 2 µg GmhB.

Bacterial Lysate Transfections and Infection.

Neisseria strains were grown overnight on GC agar supplemented with IsovitaleX enrichment (BD Biosciences). E. coli and S. typhimurium were grown overnight on LB agar, S. pneumoniae was grown on Columbia blood agar containing 5% sheep blood, and *H. influenzae, B. multivorans, L. monocytogenes*, and *S. aureus* were grown on brain heart infusion (BHI) agar (BD Biosciences). Where culture supernatant was desired, overnight cultures were scraped into PBS, re-suspended in RPMI 1% Isovitalex at an OD$_{600}$=0.2, grown for 6 hours and the spent medium filtered through a 0.22 μm filter. For heat-killed bacteria, overnight cultures were scraped into PBS and 1 OD$_{600}$ unit was re-suspended in 100 μl PBS and heated to 65° C. for 1 hr, with the exception of *B. multivorans* which was heated to 85° C. Cell pellets were washed, re-suspended in 100 μl PBS, and 2 μl/well used as treatment. To generate lysates, cultures were treated as above and boiled for 15 minutes. Insoluble components were pelleted, and the supernatant treated with RNAse A (10 μg/ml), DNAse 1 (10 μg/ml), Proteinase K (100 μg/ml). Samples were boiled for 10 minutes, insoluble material was pelleted, supernatant passed through a 0.22 μm filter, and 1 μl/well was used as a treatment. To generate transfection complexes, 1 μl lysate was mixed with 1 μl lipofectamine 2000 (Life) in 25 μl Opti-MEM, incubated for 30 minutes, and added dropwise to 293T cells at 70% confluence. For opsonization, overnight cultures of *E. coli* were washed and re-suspended at an OD$_{600}$=0.5 in 20% heat-inactivated human serum (Chemicon) for 1 hour at 25° C., then washed twice with PBS 10% FBS and added to differentiated THP-1 macrophages in antibiotic free medium, pre-treated with 10 μg/ml cytochalasin D or DMSO for 30 min, at an MOI of 5. After 1 hr, media was removed, washed, and replaced with RPMI complete media containing 50 μg/ml gentamicin.

Purification of HBP Supernatants

Purified HBP-containing (or HBP-deficient) supernatants, were isolated from spent *Neisseria* cultures essentially as described previously (Malott et al., 2013). Briefly, *N. gonorrhoeae* or *N. meningitis* wild-type or ΔhldA were grown from OD$_{550}$ 0.18 to ~0.5 for 6 hours in RPMI containing 1% Isovitalex. Supernatants were digested with DNAse (10 μg/ml), RNAse (10 μg/ml), Proteinase K (100 μg/ml), boiled for 30 minutes, passed through an Amicon 3 kDa MW cutoff filter (Millipore), and a C18 Sep-Pak® cartridge (Waters). Any residual LOS was removed using endotoxin removal resin (Pierce) according to manufacturer's instructions.

Measurement of Inflammatory Cell Death.

Cell death in THP-1 differentiated macrophages infected with live opsonized *E. coli*, HBP-containing or deficient supernatants, or transfected with LPS (Sigma) using lipofectamine 2000, were measured using the Cytotox96 cytotoxicity assay (Promega) according to manufacturer's instructions. LDH release was measured at 24 hr, and quantified as a percentage of total LDH released from lysis 100% of cells. Where indicated, LDH release from untreated cells was used for correction.

Lentivirus Production and Infection pLKO.1-based lentiviral particles were produced as previously described (Moffat et al., 2006). For each gene to be targeted, a minimum of 5 shRNAs were first tested for effective titer using Alamarblue viability assays and for gene silencing using real-time qPCR (Blakely et al., 2011). Target cells, 293T, or THP-1 monocytes were infected in media containing 8 μg/ml polybrene. 24 hours later, cells were selected with 2 μg/ml puromycin. Cells were harvested after 72 hours and knockdown efficiency was again confirmed by qPCR.

Real-Time Quantitative PCR and ELISAs

RNA was isolated using an RNeasy kit (Qiagen) per manufacturers' protocol. cDNA was synthesized using the iScript cDNA synthesis kit (Bio-Rad) and treated with TURBO DNase (Life Technologies). cDNA was amplified using SsoAdvanced SYBR Green (Bio-Rad) using a C1000 thermal cycler (Bio-Rad). Target genes were amplified using the following primers:

```
GAPDH
                                  (SEQ ID NO: 31)
5'-ttgaggtcaatgaaggggtc-3'
 and (SEQ ID NO: 32)
5'-gaaggtgaaggtcggagtca-3';

NFKBIA
                                  (SEQ ID NO: 33)
5'-tcatggatgatggccaagt-3'
and (SEQ ID NO: 34)
5'-gtcaaggagctgcaggagat-3';

CCL1
                                  (SEQ ID NO: 35)
5'-aagcaacatctggagaaggg-3'
and (SEQ ID NO: 36)
5'-atgcagatcatcaccacagc-3';

TNFA
                                  (SEQ ID NO: 37)
5'-9ccagagggctgattagaga-3'
and (SEQ ID NO: 38)
5'-tcagcctcttctccttcctg-3';

CXCL10
                                  (SEQ ID NO: 39)
5'-gcaggtacagcgtacggttc-3'
and (SEQ ID NO: 40)
5'-cagcagaggaacctccagtc-3';

IL8
                                  (SEQ ID NO: 41)
5'-agcactccttggcaaaactg-3'
and (SEQ ID NO: 42)
5'-cggaaggaaccatctcactg-3';

LUC
                                  (SEQ ID NO: 43)
5'-ctcactgagactacatcagc-3'
and (SEQ ID NO: 44)
5'-tccagatccacaaccttcgc-3'

R1P2K
                                  (SEQ ID NO: 45)
5'-ggtgaatggcacttgaaaca-3'
and (SEQ.ID.NO: 46)
5'-ggcacaaaatccagatgaaag-3';

MYD88
                                  (SEQ ID NO: 47)
5'-aaaggcttctcagcctcctc-3'
and (SEQ ID NO: 48)
5'-actgctcgagctgcttacca-3';
```

-continued

MAVS
(SEQ ID NO: 49)
5'-tcagattctggagagagggc-3'
and (SEQ ID NO: 50)
5'-ggtcgccaggtctcagg-3';

TMEM173(STING)
(SEQ ID NO: 51)
5'-atatacagccgctggctcac-3'
and (SEQ ID NO: 52)
5'-gatatctgcggctgatcctg-3'.

Relative expression was calculated using the $2^{-\Delta\Delta CT}$ method following normalization of target gene abundance to GAPDH. Quantitative measurements of cytokines were performed using ELISA kits form R&D Systems (KC, IL-23, IFN-β) or BD Biosciences (IL-1β, IL-8, IL-6, IL-12p70, TNF-α). Nuclear extracts were prepared from Jurkat T cells and NF-κB subunit binding was determined using the TransAM® Transcription Factor ELISA (Active Motif).

Microarray

Two clonal populations of Jurkat cells were stimulated for 2 hr with purified HBP-containing supernatants, or supernatants from *M. catarrhalis*. RNA was extracted using RNeasy (Qiagen), labeled using Illumina TotalPrep RNA Amplification kit (Ambion) and analyzed on a human HT-12 v4.0 Beadchip (Illumina). Data normalization and analysis were provided as a service by the Bioinformatics Department of the University Health Network (UHN) Micro array Centre, Toronto, ON. Data was analyzed using Genespring v11.0.1. Genes with a ≥1.5 fold change (FC) in gene expression in both clones when treated with HBP-containing supernatants compared to *M. catarrhalis* supernatants are shown.

Primary Cell Culture

Whole blood was taken by venipuncture from human volunteers. Peripheral blood mononuclear cells (PBMCs) were isolated using Ficoll-Paque (GE). PBMCs ($2\times10^6$ cells/ml) were incubated for one hour at 37° C. to allow monocytes to adhere. Following removal of non-adherent cells, monocytes were re-suspended and incubated for 7 days in RPMI 1640, 10% FBS, 1% glutamax, 1% penicillin streptomycin, containing 100 ng/ml recombinant human Granulocyte macrophage-colony stimulating factor (GM-CSF) (BioLegend). For infections, cells were detached using accutase (Sigma) and seeded at $2\times10^5$ cells/well in 48 well plates without antibiotics. Human neutrophils were isolated from citrated whole blood taken from healthy volunteers by venipuncture using Ficoll-Paque (GE) as described previously (McCaw et al., 2003).

Air Pouch

FvB mice (6-8 wk) were anesthetized with isoflurane, and dorsal air pouches raised by injecting 3 ml sterile air subcutaneously on day 0 and 2 ml on day 3. On day 5, air pouches were injected with 1 ml RPMI 1% isovitalX or 1 ml HBP purified from spent cultures of *N. gonorrhoeae* Wt, or ΔhldA. Mice were sacrificed 3 hr after the injection and serum samples were collected by cardiac puncture. Air pouches were washed with 2 ml PBS. Neutrophils were quantified using trypan blue exclusion. KC levels in the sera and air pouch were quantified by ELISA as described above.

Example 3—TIFA Mediated Detection of Bacterial Heptose-1,7-Bisphosphate

Germ-line encoded pattern recognition receptors (PRRs) on the plasma or endosomal membranes and others in the cytosol sense pathogen-associated molecular patterns (PAMPS), and mediate the production of pro-inflammatory cytokines via activation of the transcription factor NF-κB. Common bacterial PAMPs sensed extracellularly or on the luminal side of the phagosome, including LPS, peptidoglycan, flagellin, and CpG-containing DNA, are sensed by Toll-like receptors (TLRs)-2, -4, -5, and -9 respectively (Blasius and Beutler, 2010)(Kumar et al., 2011). In the host cytosol, peptidoglycan degradation products muramyl dipeptide and diaminopimelic acid containing muropeptides activate the NOD-like receptors (NLRs) NOD2 and NOD1 (Girardin et al., 2002), while microbial nucleic acid alerts the retinoic acid-inducible gene-like receptors (RLRs) (Yoneyama et al., 2004) or the cytoplasmic DNA sensors CDSs (Sun et al., 2013) (Wu et al., 2013). Following activation, each receptor recruits a defined set of adaptor proteins that mediate transcriptional responses through shared signaling intermediates. Proximal adaptor proteins MyD88, RIP2K, MAVS, and STING are recruited to TLRs, NLRs, RLRs and CDSs, respectively, and upon stimulation activate a shared set of signaling mediators including the tumor necrosis factor (TNF) receptor-associated factor (TRAF) family of proteins. TRAF6 specifically, is an E3 ubiquitin ligase essential for signaling downstream of the TLRs, NLRs, and RLRs, mediates Lys63 (K63)-linked ubiquitination and activation of kinases that control NF-κB and mitogen activated kinae (MAPK) transcription factors (Ferrao et al., 2012).

Heptose-1,7-bisphosphate, an intermediate in the synthesis of bacterial lipopolysaccharide, is sensed in the host cell cytosol by a mechanism that ultimately activates an NF-κB dependent inflammatory response. However, how mammalian cells are able to sense cytosolic HBP remains an open question. Here we describe novel innate immune signaling pathway, mediated by the protein TRAF-interacting forkhead associated protein A (TIFA), that can sense and respond to the presence of cytosolic HBP.

Figure 11:
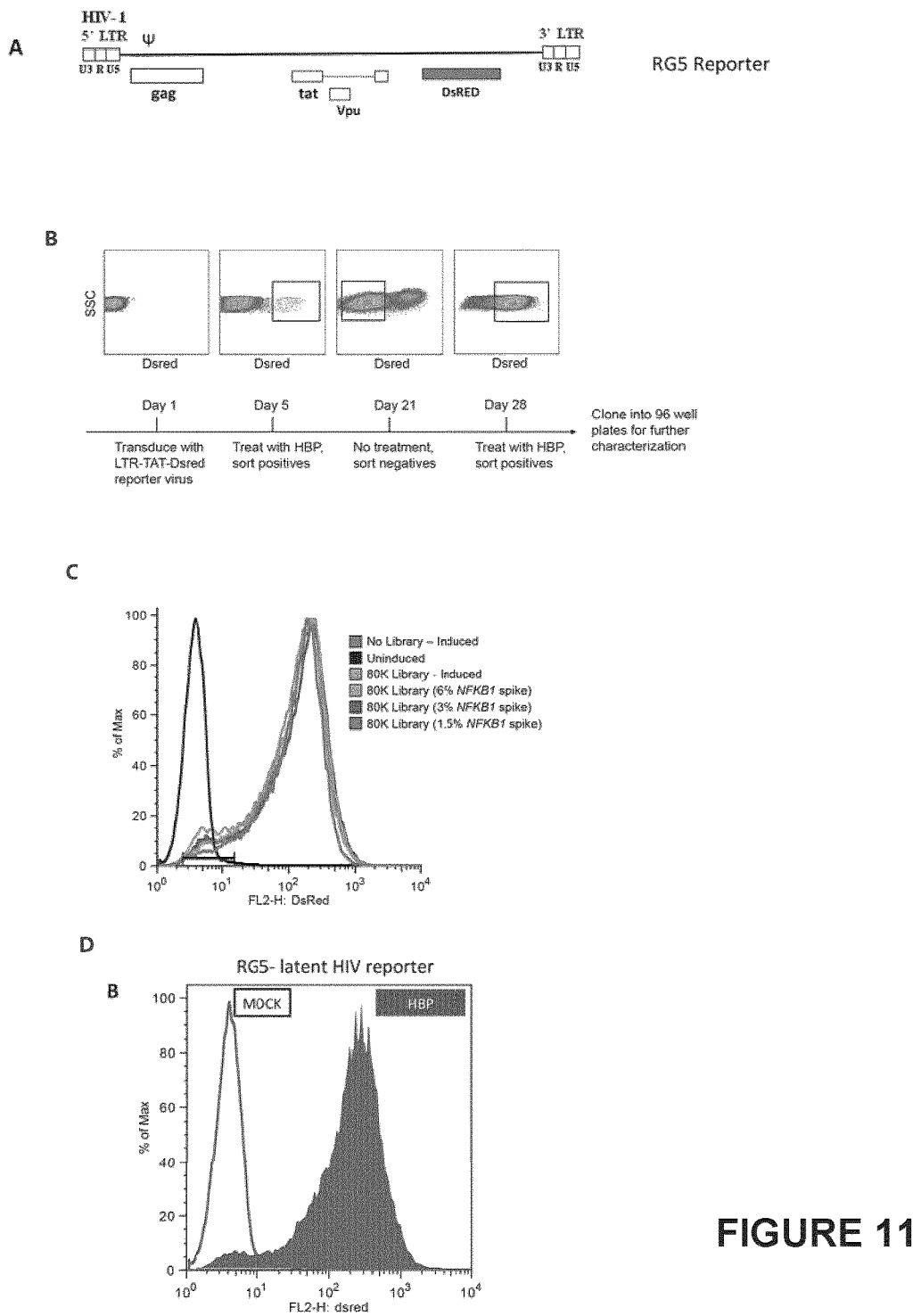
FIG. 11. Shown in FIG. 11 (A) is the construct termed RG5—the genome of HIV-1 modified to include the DsRed open reading frame in the Nef position. The construct was engineered into Jurkat T cells to generate a stable latent HIV-1 reporter cell line following successive FACS sorting of DsRed positive and DsRed negative cell populations following treatment with or without HBP shown in FIG. 11 (B).
Figure 12:
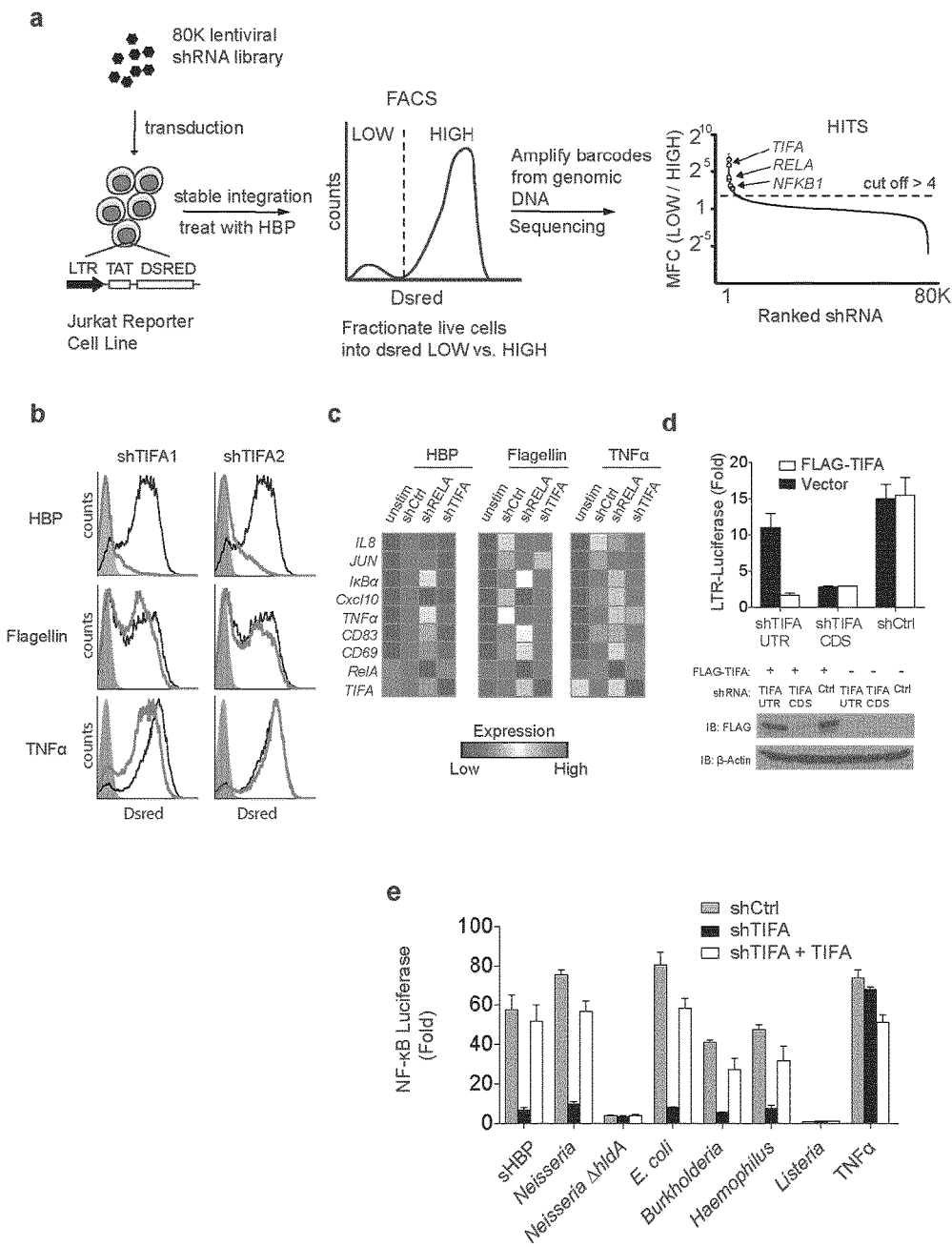
FIG. 12. Shown in FIG. 12(*a*), is a schematic of the RNAi screen used to identify HBP signaling mediators; The 78K lentiviral library was used to transduce Jurkat reporter (RG5) cells harboring a latently integrated HIV-LTR-DsRed construct. Following selection and treatment with HBP, live cells were sorted into LOW and HIGH DsRed fractions and the abundance of each hairpin in each fraction determined using Illumine sequencing. The mean fold change (MFC) of each hairpin was calculated from the normalized number of reads in the LOW and HIGH fractions from 4 replicates performed on separate days. Genes were classified as hits if >2 unique targeting shRNAs had an MFC of >4. Shown in empty circles, are the position of the two shRNAs targeting the indicated genes: NFKB1, RELA, and TIFA.
Figure 13:
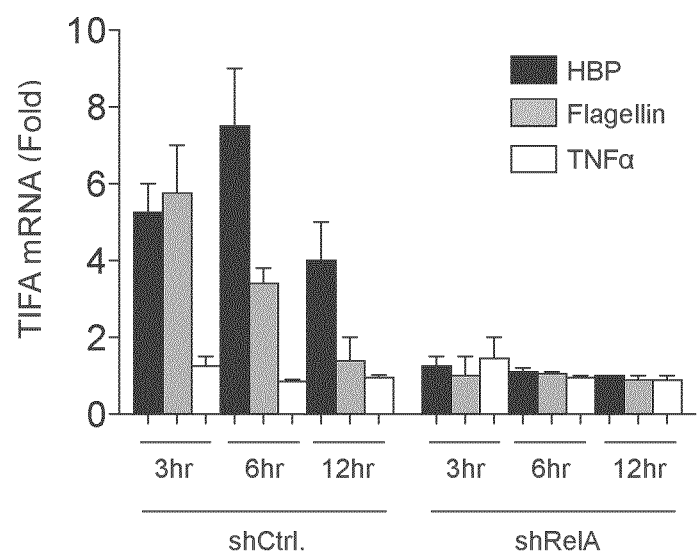
FIG. 13. Shown is qRT-PCR analysis of TIFA mRNA levels in Jurkat T cells treated with HBP, flagellin, or TNFα (after knockdown of the NF-κB subunit ReIA, or treated with a scrambled shRNA (shCtrl).

We conducted a human genome-wide RNAi screen to identify proteins that mediate the response to HBP. To maximize the RNAi phenotype, we created novel latent HIV-1 reporter Jurkat T cell lines to take advantage of a unique characteristic of LTR-driven transcription: a TAT-mediated positive feedback loop that drives phenotypic bifurcation (Weinberger et al., 2005) (FIG. 11A). HBP was able to potently induce HIV gene expression from latently-infected cells (FIG. 11B). Notably, anti-latency compounds offer the potential of purging the latent reservoir as part of a combinational therapy for HIV treatment (Moreno, 2012). We then optimized screening conditions by titrating an NFKB1-specific small hairpin RNA (shRNA) into a lenti-viral pool containing 78 000 (78K) unique sequences, and monitored HBP-mediated LTR-DsRed expression following transduction. Using these conditions, we transduced the reporter-containing cell line with a pooled genome-wide shRNA library so that less than one in three cells were transduced, and then used fluorescence-activated cell sorting (FACS) to fractionate live cells into DsRed LOW (<5%) and HIGH (>95%) expressing fractions following HBP treatment. Hits were defined as genes with at least 2 targeting hairpins found at a 4-fold greater frequency in the LOW vs. HIGH fractions following sequencing of hairpin barcodes amplified from the genomic DNA. NFKB1 and RELA, known to be required for HBP-mediated LTR activation, were both identified as hits, validating the screen (FIG. 9a). To identify HBP specific signaling regulators, we chose the top 10 scoring genes after filtering out general cellular machinery and conducted a secondary screen assessing the respective proteins' involvement in other NF-κB signaling pathways, specifically TLR5 and TNFR. Of these 10, TRAF-interacting forkhead associated protein A (TIFA), a ubiquitously expressed cytoplasmic protein known to activate NF-κB in 293 cells (Kanamori et al., 2002) (Takatsuna et al., 2003), was uniquely required for HBP signaling, as 2 non-overlapping sequence-targeting hairpins abrogated HBP-mediated DsRed expression, while showing little effect on flagellin and TNFα-driven expression (FIG. 12b). Furthermore, TIFA knockdown specifically attenuated the HBP induced pro-inflammatory transcriptional response 2 hours post treatment (FIG. 12c). We then rescued the RNAi phenotype by creating cell lines expressing a recombinant FLAG epitope-tagged TIFA and then treating these with an shRNA targeting the 3' UTR absent in the recombinant construct (FIG. 12d). Moreover, TIFA knockdown abrogated Gram-negative lysate-mediated NF-κB activation, without affecting the cellular responses to TNFα in 293T cells (FIG. 12e). Importantly, this phenotype could be rescued by stable expression of FLAG-TIFA (FIG. 12e). Notably, measuring NF-κB driven luciferase in HBP-treated 293T cells in which TIFA is expressed versus in cells in which TIFA has been depleted offers the potential of identifying additional activators of the TIFA-signaling axis. TIFA expression itself was upregulated over 5-fold following HBP treatment, and this was dependent on RelA (FIG. 13), suggesting a positive feedback loop for TIFA expression to maintain the signal induced by HBP. These results implicate TIFA as an essential component of the HBP signaling pathway.

Figure 14:
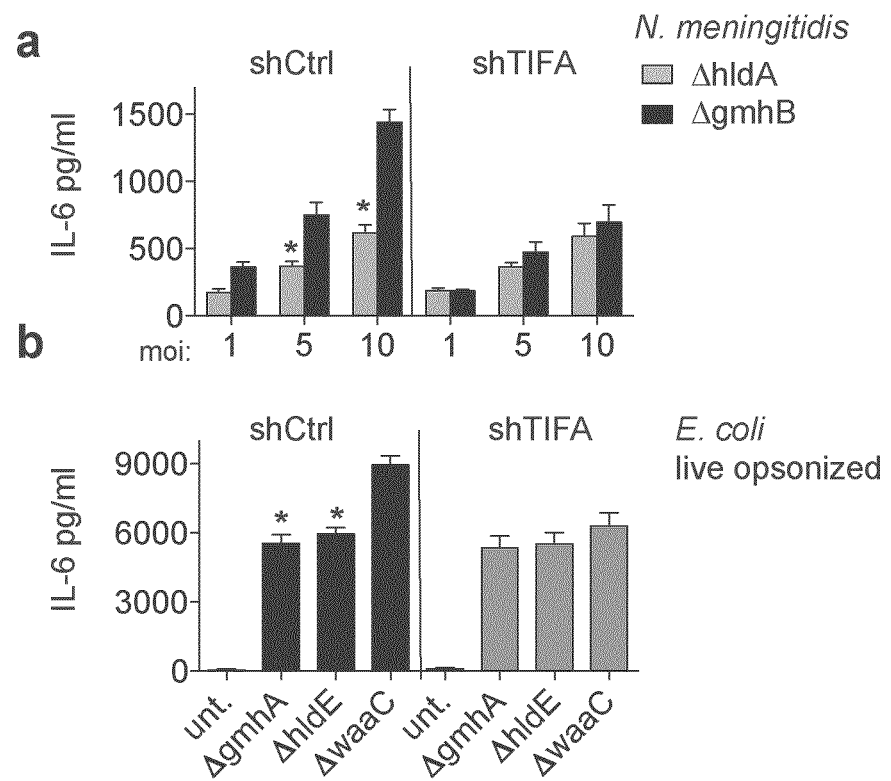
FIG. 14. Shown in FIG. 14(*a*) is TIFA knockdown and IL-6 production in THP-1 macrophages infected with live *N. meningitis* (6 hr) or live-opsonized *E. coli* (24 hr) (FIG. 14(*b*)) of the indicated genotype by ELISA.
Figure 15:
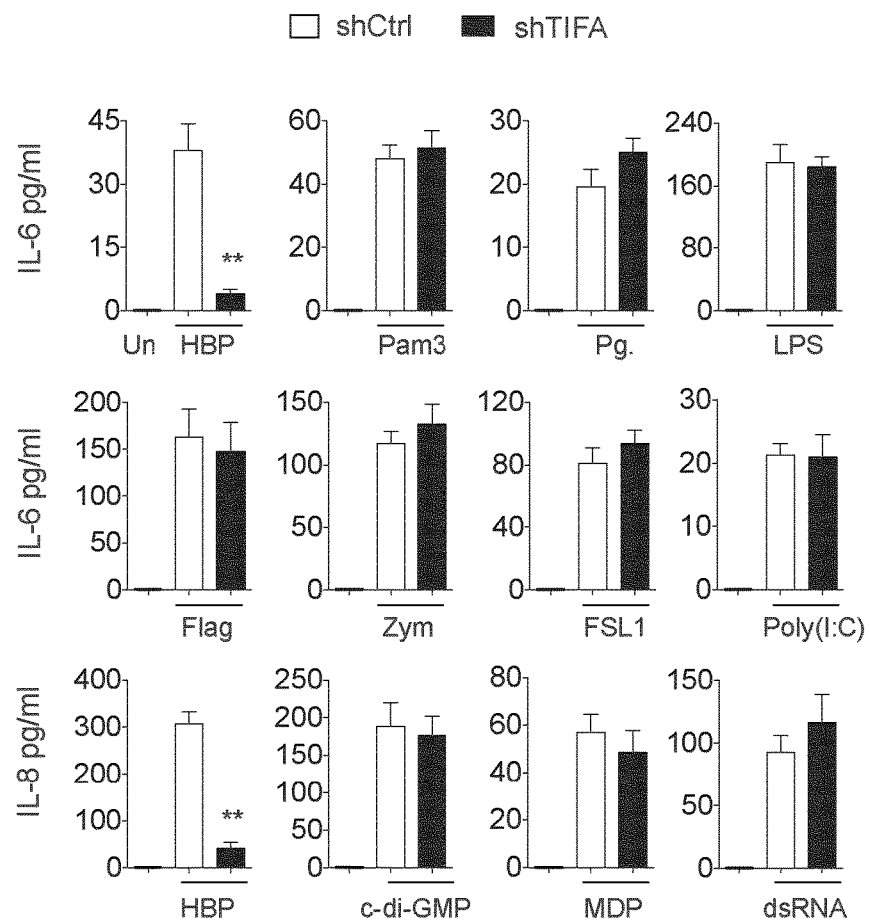
FIG. 15. ELISA of IL-6 (top two rows) or IL-8 (bottom row) secreted from THP-1 macrophages expressing TIFA or scrambled shRNA and treated with the indicated pathogen-associated molecular pattern (PAMP) ligand for 6 hr; Pam3SK4 (Pam3), *N. gonorrhoeae* derived peptidoglycan (Pg.), flagellin (Flag), zymosan (Zym), muramyl dipeptide (MDP). Data are from 3 independent experiments (error bars s.e.m). **P<0.01.

TIFA knockdown prevented the increase in IL-6 following infection of THP-1 macrophages with wild type *N. meningitis* or live opsonized *E. coli*, both of which are capable of synthesizing HBP (FIG. 14a, b). TIFA knockdown also abrogated IL-6 and IL-8 production in THP-1 macrophages otherwise seen upon HBP treatment (FIG. 15). However, this effect was remarkably specific for HBP, as TIFA was completely dispensable for macrophages to respond to a variety of other PAMPs of bacterial and viral origin (FIG. 15). Thus, TIFA is an essential component of a unique HBP signaling pathway.

Figure 16:
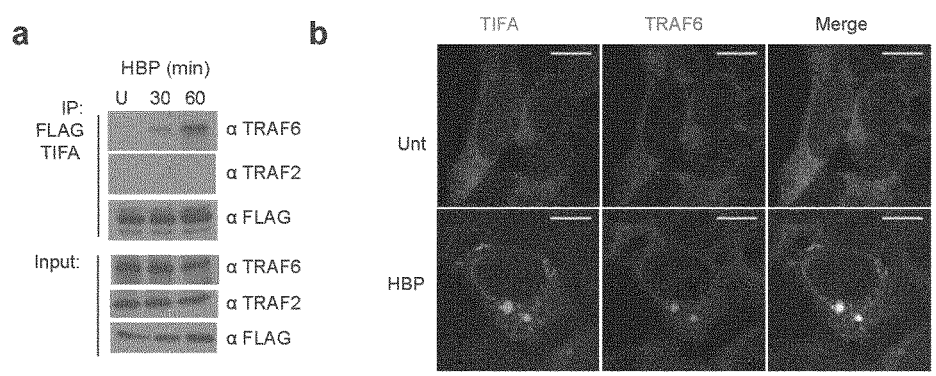
FIG. 16. Shown in FIG. 16(*a*) is immunoprecipitation (IP) of FLAG-TIFA in Jurkat cells with HBP-containing or deficient supernatant, and immunoblot for TRAF6TRAF2, or FLAG-TIFA (2 hr).
Figure 17:
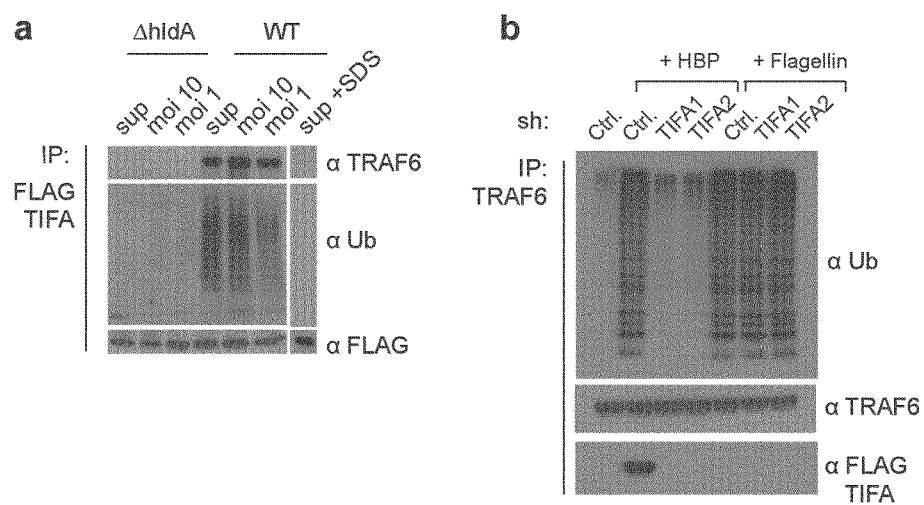
FIG. 17. Shown in FIG. 17(*a*) is Immunoprecipitation (IP) of FLAG-TIFA and immunoblot of TRAF6, FLAG-TIFA, or ubiquitin, in Jurkat cells treated with HBP-containing or deficient supernatant (sup), or infected with *N. gonorrhoeae* of the indicated genotype and MOI (2 hr).
Figure 18:
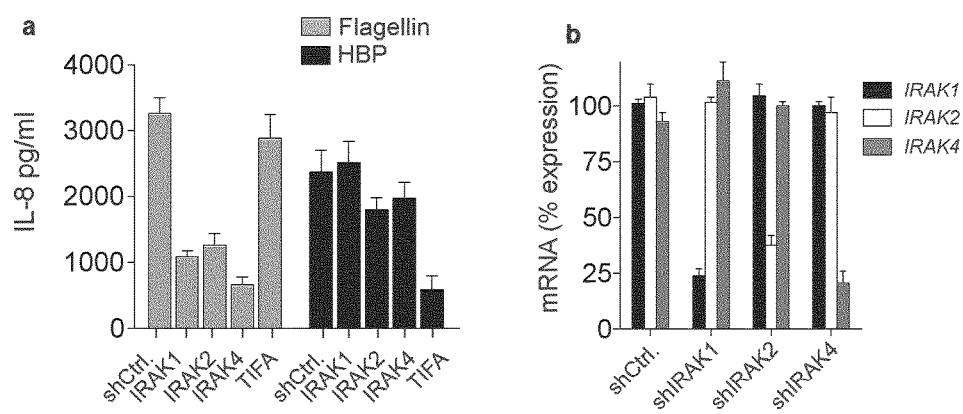
FIG. 18. Shown in FIG. 18(*a*) is shRNA knockdown of IRAK1, IRAK2, or IRAK4 and IL-6 production in THP-1 macrophages treated with HBP-containing supernatants, or flagellin (24 hr).

TIFA overexpression studies suggest that TIFA-mediated NF-κB activation occurs via activation of the ubiquitin ligase TRAF6 (Ea et al., 2004). Despite the fact that TRAF6 is essential for TLR- and IL-1R-mediated NF-κB activation, studies have yet to identify any agonist of TIFA or a role for TIFA in any physiologically relevant cellular response. To determine if HBP has an effect on the TIFA-TRAF6 interaction, we created stable Jurkat and 293T cell lines expressing FLAG-TIFA from an MSCV promoter and knocked down endogenous TIFA using a TIFA-UTR targeting shRNA. In this system, the TIFA-TRAF6 interaction was completely dependent on HBP, and was apparent as early as 30 min post treatment (FIG. 16a). No interaction was observed with TRAF2, another proposed TIFA binding partner (Kanamori et al., 2002). Immunostaining indicated that TIFA co-localized with TRAF6 in distinct foci upon HBP treatment (FIG. 16b). The formation of such large, oligomeric TRAF6 complexes is required to activate its E3 ubiquitin ligase activity, and occurs similarly following recruitment to TLR or IL-1R signalosomes (Ferrao et al., 2012). Ubiquitin chains could be detected in both the *N. gonorrhoeae* infected, or HBP induced, TIFA-TRAF6 complex following TIFA immunoprecipitation, indicating the ubiquitin ligase activity of TRAF6 was being activated (FIG. 17a). This was TIFA-dependent, as TIFA depletion abrogated HBP-mediated TRAF6 ubiquitination, whereas TLR5-mediated ubiquitination of TRAF6 was unaffected (FIG. 17b). TRAF6 is recruited to the TLR and IL-1R signalosomes by the IRAK family of serine and threonine kinases. Yet, RNAi depletion indicated HBP signals independently of IRAK1, -2, and -4 (FIG. 18a, b). Therefore, TIFA is a novel entry point into the TRAF6-mediated NF-κB activation pathway downstream of HBP.

Figure 19:
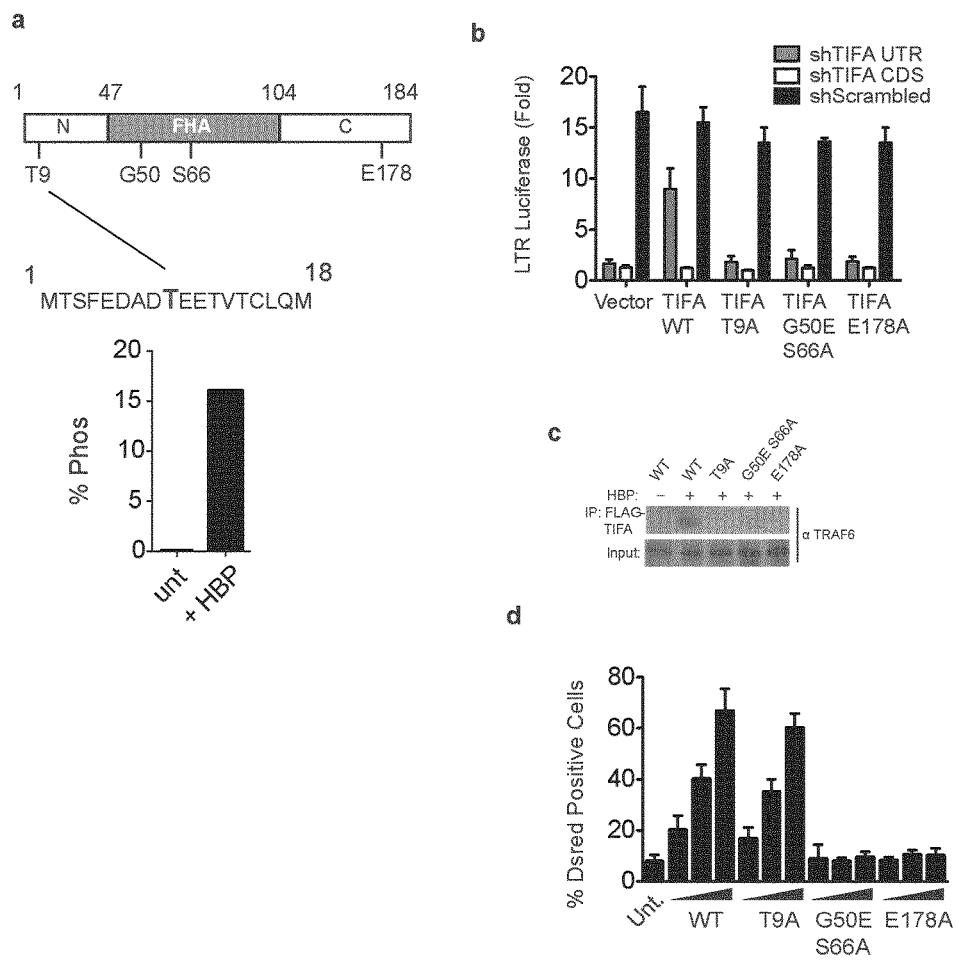
FIG. 19. Shown in FIG. 19(*a*) is a depiction of the primary structure of TIFA and quantification of a phospho-threonine 9 (pT9) peptide of FLAG-TIFA immunoprecipitated from stable 293T cells with or without HBP treatment.
Figure 20:
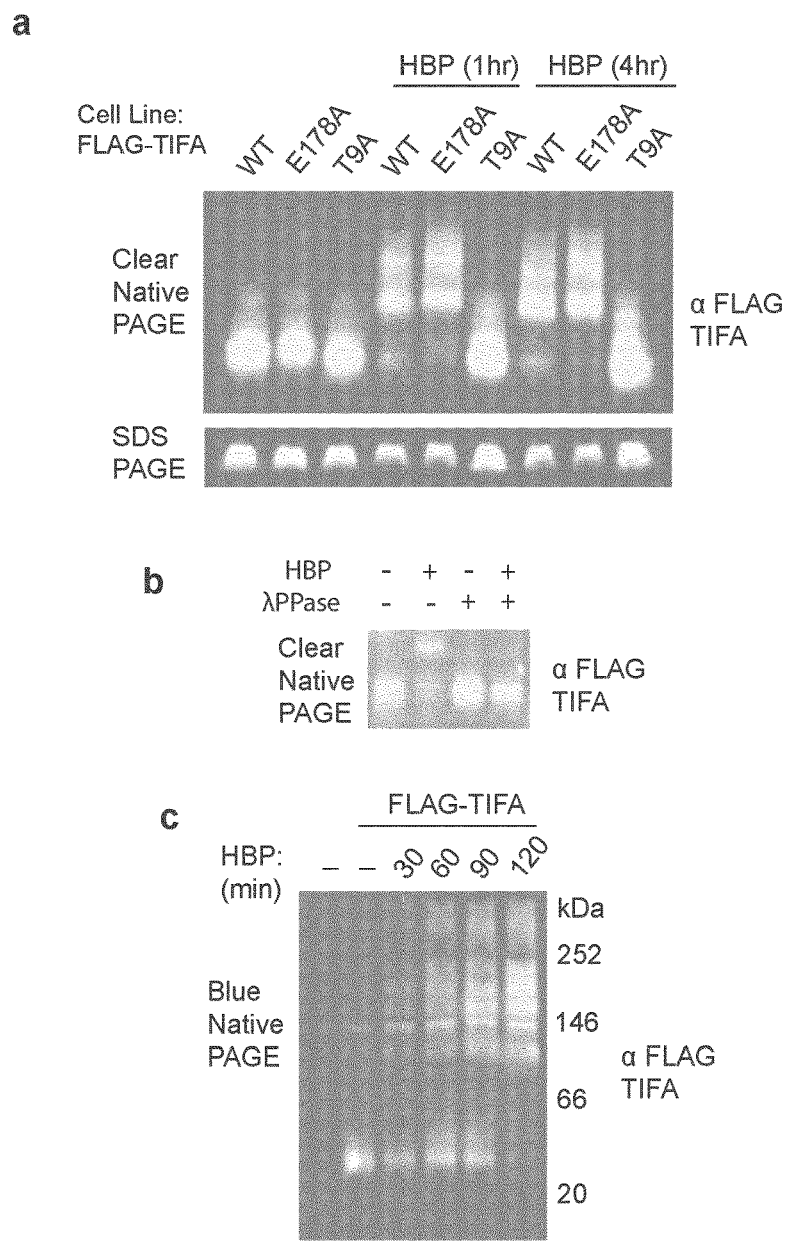
FIG. 20. Shown in FIG. 20(a) is clear native PAGE (top) or SDS-PAGE (bottom) and immunoblot analysis of Jurkat cells stably expressing the indicated FLAG-TIFA construct, transduced with a TIFA 3' UTR specific shRNA, and treated with HBP.

It has been previously shown that TIFA over-expression results in self-association via constitutive phosphorylation at threonine-9 (pT9) leading to oligomerization via intermolecular pT9 binding with the central forkhead-associated domain (FHA) (Huang et al., 2012). We hypothesized that constitutive TIFA phosphorylation and oligomerization previously observed were a result of overexpression, and is in fact, a HBP-specific signaling mechanism. To test this, FLAG-TIFA was immunoprecipitated and analyzed by LC-MS/MS from HBP, or mock-treated Jurkat cells stably expressing FLAG-TIFA. Indeed, Thr9 was phosphorylated only after treatment with HBP (FIG. 19a). Furthermore, cells treated with the TIFA-UTR-specific hairpin and re-constituted with recombinant TIFA T9A, TIFA containing conserved mutations in the FHA domain (G50E/S66A), or TIFA containing a mutation in the TRAF6 binding site (E178A), were unresponsive to HBP treatment (FIG. 19b), nor could they bind TRAF6 in a HBP-dependent manner (FIG. 19c). T9 phosphorylation appears to be a HBP trigger, as upon over-expression in HEK293T cells, the T9A mutant can still activate the HIV LTR when co-transfected, whereas the FHA (G50E/S66A), and TRAF6 (E178A) mutants cannot (FIG. 19d). HBP also triggered TIFA oligomerization when analyzed by clear native-PAGE (FIG. 20a,b) or blue native PAGE (FIG. 20c), in a process independent of TRAF6 binding, but completely dependent on Thr9 phosphorylation. Thus, HBP induces phosphorylation of TIFA Thr9, triggering intermolecular binding between TIFA pT9- and TIFA-FHA leading to oligomerization and subsequent TRAF6 activation.

Figure 21:
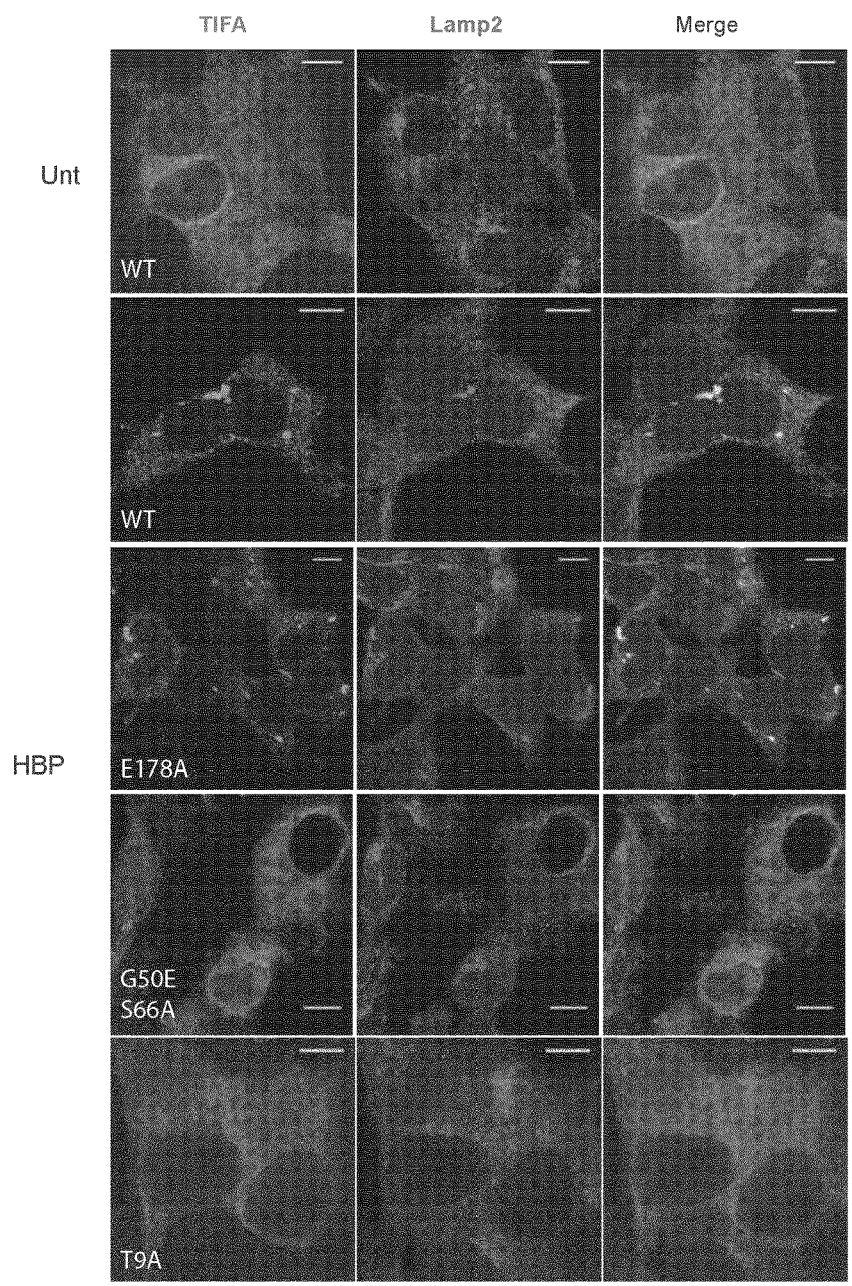
FIG. 21. Shown is confocal microscopy of FLAG-TIFA and Lamp2 in HEK 293T cells stably expressing the indicated FLAG-TIFA construct, transduced with TIFA 3' UTR specific shRNA, and treated with HBP (4 hr). Scale bars, 10 μm. Data are representative of at least 3 independent experiments.

Given that soluble HBP gains access to the cytosol via endocytosis, and that phagocytosis of *E. coli* liberated pro-inflammatory HBP in macrophages, we hypothesized that lysosomes may play a role in mediating TIFA signaling. Treatment of 293 cells with soluble HBP induced the formation of large TIFA aggregates or "TIFAsomes" that co-localized with the late endosomal/lysosomal maker Lamp2 (FIG. 21). This was independent of TRAF6 binding, but was dependent on Thr9 phosphorylation and a functional FHA domain, as HBP-induced TIFAsomes were evident in cells re-constituted with TIFA E178A but not TIFA T9A or G50E/S66A. Thus, HBP treatment induces TIFA phosphorylation dependent complex formation at the lysosome.

Together these results indicate that HBP is a novel PAMP detected in the host cytosol, activating an NF-κB dependent immune response via a TIFA-dependent process. That HBP is detected in the cytosol of such a wide variety of human cells, primary and transformed, immune and non-immune, indicated the presence of a previously unknown innate immune surveillance pathway. Consistent with TIFA being a proximal protein in the sensing of HBP, HBP-induced TIFA signaling complexes could be found at the lysosome, where HBP initially gains access to the cytosol. HBP-dependent activation stimulates TIFA phosphorylation, oligomerization and activation of the ubiquitin ligase TRAF6, which leads to the activation of NF-κB-dependent transcription. Considering that all other innate immune adaptor proteins are not essential for HBP-detection, TIFA is the key to linking cellular detection of HBP with the common PAMP signaling hub TRAF6.

Methods
Cell Culture, Luciferase Assays 293T were maintained in DMEM supplemented with 10% FBS, 1% glutamax, and 1% penicillin streptomycin. Jurkat 1G5 cells contain a stably-integrated LTR-luciferase reporter gene (Aguilar-Cordova et al., 1994), and were maintained in RPMI supplemented with 10% FBS and 1% glutamax. THP-1 cells were maintained in RPMI supplemented with 10% FBS and 1% glutamax and differentiated to macrophages with 50 ng/ml PMA for 48 hr, followed by a 48 hr rest period prior to stimulation. To measure LTR-driven luciferase, 1G5 cells were lysed and luminescence determined using the Luciferase Assay kit (Promega) according to manufacturers instructions. Results are expressed as fold change compared to untreated. 293T cells were transfected in 96 well plates with 90 ng ELAM firefly luciferase reporter plasmid (Chow et al., 1999) and 10 ng pRL-TK Renilla plasmid using TransIT LTI (Mirus). 18 hours later cells were treated for 6 hours and luciferase activity determined using the Dual-Glo Luciferase Assay System (Promega). Results are expressed as fold increase relative to transfected, mock treated cells following normalization to *Renilla* luciferase.

Purification of HBP Supernatants

Purified HBP-containing (or HBP-deficient) supernatants, were isolated from spent *Neisseria* cultures essentially as described previously (Malott et al., 2013). Briefly, *N. gonorrhoeae* or *N. meningitis* wild-type or ΔhldA were grown from $OD_{550}$ 0.18 to ~0.5 for 6 hours in RPMI containing 1% Isovitalex. Supernatants were digested with DNAse (10 µg/ml), RNAse (10 µg/ml), Proteinase K (100 µg/ml), boiled for 30 minutes, passed through an Amicon 3 kDa MW cutoff filter (Millipore), and a C18 Sep-Pak® cartridge (Waters). Any residual LOS was removed using endotoxin removal resin (Peirce) according to manufacturer's instructions.

Reporter Cell Line Generation.

The full-length HIV-1 molecular clone pLAI containing the following modifications was used as the reporter backbone: AvrII deletion of the 3' end of Gag and the entire coding sequence of Pol, and a the NdeI/StuI deletion of the 3' end of Env. The Dsred allele was cloned into the Nef reading frame using BamH1, and XhoI. Lentiviral particles were produced by co-transfection into 293T cells with pMDG.2 and psPAX2. Jurkat cells were transduced with the minimum dose required to see DsRed positive cells following treatment with 10 ng/ml TNFα. 48 hours post transfection, cells were treated HBP, and DsRed positive cells sorted by FACS. Cells were cultured for 14 days followed by DsRed negative cell sorting by FACS. 5 days later, cells were induced with HBP, and DsRed positive cells collected into 96 well plates (0.5 cells/well). Clones were individually tested for low basal DsRed expression, and high DsRed expression following treatment with both HBP and TNFα and termed RG5.

Pooled Lentiviral shRNA Screen.

A pooled lentiviral shRNA library containing 78,432 shRNAs targeting 16,056 Refseq Human genes ("80K library") developed by the RNAi consortium (Moffat et al., 2006), and described previously (Marcotte et al., 2012) was used to transduce $1.2 \times 10^8$ Jurkat-RG5 cells at an MOI of 0.3 resulting in 1500 fold coverage of each hairpin. 24 hours later, cells were re-suspended in complete RPMI containing 4 µg/ml puromycin. Following 3 days of selection, dead and early apoptotic cells were removed using a dead-cell removal kit (Miltenyi Biotec). 24 hours later, $\sim 2 \times 10^8$ cells were treated with HBP-containing supernatant and incubated for 48 hours in the presence of 2 ug/ml puromycin. Cells were stained with APC-Annexin V (BD Biosciences), and $5 \times 10^6$ APC-negative cells from both the lowest 5% of the DsRed expressing population, and highest 95% expressing DsRed population were collected. The process was repeated on successive days for a total of 4 replicates. Genomic DNA was harvested using a Qiagen DNEAsy Kit, precipitated, and re-suspended at 400 ng/ml in $H_2O$. shRNA barcodes were amplified by PCR, subject to Illumina sequencing and analyzed as described previously (Ketela et al., 2011). Data were normalized to reads per million reads and a threshold was set to 0.1 reads/million reads. The MFC (mean fold change) was determined for each hairpin by dividing the mean number of reads from the DsRed LOW fraction by the mean number of reads in the DsRed HIGH fraction.

Flow Cytometry

Live cells were re-suspended to $1 \times 10^6$ cells/ml in 2% FBS in PBS and analyzed using a FACSCalibur with CellQuest software (Becton Dickinson). Analysis was preformed using FlowJo software (TreeStar). Cell sorting was done using an Aria I cell sorter (Becton Dickinson).

Confocal Microscopy

HEK 293T cells were seeded on collagen coated glass coverslips, treated for 4 hr with HBP, fixed with 4% paraformaldehyde, and permeabilized with 0.1% saponin. For visualization of FLAG-TIFA and TRAF6, cells were stained overnight at 4° C. with Alexa Fluor-488 conjugated rabbit anti-FLAG (Cell Signaling) and mouse anti-TRAF6 (sc-8409; Santa Cruz), followed by 1 hour with Alexa Fluor-594 conjugated anti mouse (Life Technologies). For visualization of FLAG-TIFA and Lamp2, cells were stained overnight at 4° C. with mouse anti-FLAG (M2; Sigma) and rabbit anti-Lamp2 (ab37024; Abcam), followed by 1 hour with Alexa Fluor-488 conjugated anti-mouse (Life Technologies) and Alexa Fluor-594 conjugated anti-rabbit (Life Technologies). Slides were visualized using an LSM510 (Carl Zeiss) confocal microscope. For analysis, images were processed using ImageJ software FLAG-TIFA Constructs and Cell Line Generation The TIFA coding sequence was amplified from cDNA derived from Jurkat cells and cloned into pMSCV-Blast (Clonetech) containing one N-terminal FLAG sequence. Point mutations were inserted using QuickChange II mutagenesis kit (Agilent). Infectious virus was produced using the Pantropic Retroviral Expression System (Clonetech). Viral titres were determined as above using AlamarBlue viability and target cells were infected at an MOI of 0.5 as described for lentivirus infections. Cells were then selected for 14 days with blasticidin to create polyclonal stable cell lines.

Mouse Challenge

Groups of ten eight week old FVB male mice (Charles River) were challenged on day 0 and day 21 with a non-lethal dose of *N. meningitis* strain B16B6 ΔgmhB or ΔhldA. To prepare each inoculum, bacteria were grown overnight on GC agar containing 60 µg/ml kanamycin, resuspended in BHI broth, adjusted to an optical density of 0.1 and grown at 37° C. with shaking. After two hours, bacteria were diluted in sterile PBS such that each 200 µl aliquot contained $1 \times 10^6$ CFU. Mice were anesthetized with isofluorane and injected intraperitoneally with each inoculum. Without addition of an exogenous iron source, this dose of bacteria is cleared quickly from the bloodstream (<12h) and results in no sustained infection, clinical symptoms or lethality. Mice were monitored at least once per day for two days after bacterial challenge for changes in weight or clinical symptoms. No animals showed any signs of clinical illness. Whole blood was collected via facial vein bleed at the indicated time point for analysis of serum antibodies and to ensure bacterial clearance. Animal experiments were conducted in accordance with the Animal Ethics Review Committee of the University of Toronto.

Immunoprecipation and Immunobloting

FLAG-TIFA was immunoprecipitated from Jurkat cells using FLAG M2 agarose beads (Sigma) as described previously (Chen and Gingras, 2007). Briefly, cells were lysed in 50 mM Hepes-KOH pH 8.0, 100 mM KCl, 2 mM EDTA, 0.1% NP40, 10% glycerol. Soluble cell lysates were pre-cleared for 2 hr with mouse IgG agarose (Sigma) and immunoprecipitated overnight at 4° C. Proteins eluted using 0.5 M NH$_4$OH pH 11 (for mass-spectrometry), or 3× FLAG-peptide (Sigma) (immunoblot analysis). TRAF6 was immunoprecipitated from Jurkat cell lysates using rabbit anti-TRAF6 (sc-72201; Santa cruz) conjugated to protein A/G PLUS-agarose (Santa cruz) and eluted in sample buffer. Whole cell lysates or immunoprecipitation eluates were immunoblotted with the following antibodies: M2 anti-FLAG (Sigma), rabbit anti-FLAG (Sigma), mouse anti-TRAF6 (sc-8409; Santa Cruz), rabbit anti-TRAF2 (sc-876), mouse anti-ubiquitin (sc-8017; Santa cruz), mouse anti-beta actin (Sigma). For phosphopeptide analysis, FLAG-TIFA was excised from the gel, subject to in-gel trypic digestion, followed by treatment with cyanogen bromide (Sigma) in 70% TFA and analyzed by LC/MS/MS. Data were analyzed by Scaffold PTM (Proteome).

Native PAGE

For BlueNative PAGE, cells were lysed in 1% NP-40, 0.1% Triton-X100, 0.1% SDS and soluble lysate separated by gradient PAGE (8-16%) using ExpressPlus System™ (GenScript) as described previously (Kofoed and Vance, 2013). For ClearNative PAGE, cells were lysed in 1% NP-40, 0.1% Trition-X100, 0.1% SDS and soluble lysate separated on 12.5% tris-glycine polyacrylamide gels.

SUMMARY OF SEQUENCES

SEQ.ID.NO: 1 sets forth the polynucleotide sequence encoding a human TIFA polypeptide.

```
Atgaccagttttgaagatgctgacacagaagagacagtaacttgtctccag
atgacggtttaccatcctggccagttgcagtgtggaatatttcagtcaata
agttttaacagagagaaactcccttccagcgaagtggtgaaatttggccga
aattccaacatctgtcattatacttttcaggacaaacaggtttcccgagtt
cagtttctctgcagctgtttaaaaaattcaacagctcagttctctcctttt
gaaataaaaatatgagtaaaaagaccaatctgatcgtggacagcagagag
ctgggctacctaaataaaatggacctgccatacaggtgcatggtcagattc
ggagagtatcagtttctgatggagaaggaagatggcgagtcattggaattt
tttgagactcaatttatttatctccaagatcactcttgcaagaaaacaac
tggccaccacacaggcccataccggagtatggcacttattcgctctgctcc
tcccaaagcagttctccgacagaaatggatgaaaatgagtca
```

SEQ.ID.NO: 2 sets forth the amino acid sequence of the human TIFA polypeptide.

```
MTSFEDADTEETVTCLQMTVYHPGQLQCGIFQSISFNREKLPSSEVVKF
GRNSNICHYTFQDKQVSRVQFSLQLFKKFNSSVLSFEIKNMSKKTNLIV
DSRELGYLNKMDLPYRCMVRFGEYQFLMEKEDGESLEFFETQFILSPRS
LLQENNWPPHRPIPEYGTYSLCSSQSSSPTEMDENES
```

SEQ.ID.NO: 3 sets forth the polynucleotide sequence of gmhA of *Neisseria meningitidis*.

```
atgacgacattacaagaacgcgttgccgcccattttgccgaaagcatccgt
gccaagcaggaagccggaaaagtattggtcgagccgaccgtacaggctgcc
gagctgatgctgcaatgcctgatgaatgacggcaaaatcctggcctgcggc
aacggcggttcggctgccgacgcgcaacacttcgccgccgaaatgaccggc
cgttttgaaaaagaacgcatggaactcgccgctgtcgcgctgacaacagac
acttccgcgctgacagccatcggcaacgactacggtttcgaccacgtattc
agcaaacaggtgcgcgcgctcggacgtgcaggcgatgtattggtcggcatt
tccacctccggcaattccgccaacgtcatcgaagccgtcaaagccgcacac
gaacgcgatatgcacgtcatcgccttgaccggccgcgacggcggcaaaatc
gccgccatactcaaagacaccgacgtttttgctcaacgttccccatccgcgc
accgcccgtattcaagaaaaccacatcctgctgatacacgccatgtgcgac
tgtatcgactccgtactgctggaaggaatgtaa
```

SEQ.ID.NO: 4 sets forth the polynucleotide sequence of gmhA of *Escherichia coli*.

```
atgtaccaggatcttattcgtaacgaactgaacgaagcggcggaaacgctg
gctaacttttaaaagatgacgccaatattcacgccattcagcgcgcggcg
gtcctgttagcagacagctttaaagccggtggcaaagtgctttcctgcggc
aacggcggttcccattgcgacgctatgcactttgccgaagagttgaccggt
cgctaccgtgaaaaccgtccgggctaccggcgattgctatttctgacgtt
agtcatatttcctgcgtcggtaatgatttcggtttcaatgatattttctcc
cgctacgttgaagcggtaggtcgcgaaggcgatgtactgctggggatctcc
acctccggtaactctgcaaacgtgatcaaagcgatcgcagggcgcgtgag
aagggaatgaaagtgatcaccctgaccggtaaagacggcggcaaaatggct
ggcacggcggatatcgaaattcgcgtaccgcactttggttatgccgaccgc
attcaggagattcacattaaagtgatccatatcctgatccagttgattgaa
aaagagatggttaagtaa
```

SEQ.ID.NO: 5 sets forth the polynucleotide sequence of hidA of *Neisseria meningitidis*.

```
atgtccgccaagttccaacaagaaaccctcaaatcccgtttcgcgcaagcc
aaagtcctggttgtcggcgacgtgatgctcgaccgctattggttcggcgat
gtgtcccgtatttcgcccgaagccccgtgccggtggcgaaaatcggacga
atcgaccaacgcgcgggcggagcggcaaatgtcgcgcgcaacatcgcttcg
```

```
ttgggcggcagggcagggctgttgtccgtaaccggcaacgacgaagccgcc gacgcgctcgatgcgctgatggtgcaggacggcgtcgcctcctatctgatg cgcgacaaacaaatcgccaccaccgtcaaactgcgcgtcgtcgcccgcaac cagcagcttatccgtcttgattttgaagaacatcccaactgcgaagtgttg gaacaaatcaagcagaaataccgcgaaatcttgcccgaatacgacgcaatc attttttcagactacggcaaaggcggcctgtcgcatatctccgatatgatc gattgggcgaaacacgccggcaaaaccgtcttaatcgacccaaaggcgac gattacgaaaaatatgtcggtgcaactctgattacgcctaaccgcgccgaa ttgaaagaagtggtcggcagttggaaaaacgaaagcgagctgaccgaaaaa gcgcaaaacctgcgccgccacctcgacctgaccgccgttttactgaccga agcgaagaaggcatgaccttgttcagcgaaggcgaaccgatttaccagccc acccgcgcccaagaagtttacgacgtatccggtgcgggtgacaccgtcatt gccggaatgggcttgggtttggcggcaggctgcaccatgcccgaagccatg taccttgccaatactgcggccggggttgtcgtggcgaaactcggtacggcg gtttgctcgtttgccgaattgatcaaggcattgtcagggcaatcaacaatg tag
```

SEQ.ID.NO: 6 sets forth the polynucleotide of hldE of *Escherichia coli*.

```
atgaaagtaacgctgccagagtttgaacgtgcaggagtgatggtggttggt gatgtgatgctggatcgttactggtacggccccaccagtcgtatctcgccg gaagcgccggtgcccgtggttaaagtgaataccatcgaagaacgtccgggc ggcgcggctaacgtggcgatgaatatcgcttctctcggtgctaatgcacgc ctggtcgggttgacgggcattgacgatgcagcgcgcgcgctgagtaaatct ctggccgacgtcaacgtcaaatgcgacttcgtttctgtaccgacgcatccg accattaccaaattacgggtactttcccgcaaccaacagctgatccgtctg gatttgaagaaggtttcgaaggtgttgatccgcagccgctgcacgagcgg attaatcaggcgctgagttcgattggcgcgctggtgctttctgactacgcc aaaggtgcgctggcaagcgtacagcagatgatccaactggcgcgtaaagcg ggtgttccggtgctgattgatccaaaaggtaccgattttgagcgctaccgc ggcgctacgctgttaacgccgaatctctcggaatttgaagctgttgtcggt aaatgtaagaccgaagaagagattgttgagcgcggcatgaaactgattgcc gattacgaactctcggctctgttagtgacccgttccgaacagggtatgtcg ctgctgcaacccgggtaaagcgccgctgcatatgccaacccaagcgcaggaa gtgtatgacgttaccggtgcgggcgacacggtgattggcgtcctggcggca acgctggcagcgggtaattcgctgaagaagcctgcttctttgccaatgcg gcggctggcgtggtggtcggcaaactgggaacctccacggtttcgccgatc gagctggaaaatgctgtacgtggacgtgcagatacaggctttggcgtgatg accgaagaggaactgaagctggccgtagcggcagcgcgtaaacgtggtgaa aaagtggtgatgaccaacggtgtctttgacatcctgcacgccgggcacgtc tcttatctggcaaatgcccgcaagctgggtgaccgcttgattgttgccgtc
```

```
aacagcgatgcctccaccaaacggctgaaagggattcccgcccggtaaac ccactcgaacagcgtatgattgtgctgggcgcactggaagcggtcgactgg gtagtgtcgtttgaagaggacacgccgcagcgcttgatcgccgggatcttg ccagatctgctggtgaaaggcggcgactataaaccagaagagattgccggg agtaaagaagtctgggccaacggtggcgaagtgttggtgctcaactttgaa gacggttgctcgacgaccaacatcatcaagaagatccaacaggataaaaaa ggctaa
```

REFERENCES

Adams, S. (2009). Toll-like receptor agonists in cancer therapy. Immunotherapy 1, 949-964.

Aguilar-Cordova, E., Chinen, J., Donehower, L., Lewis, D. E., and Belmont, J. W. (1994). A sensitive reporter cell line for HIV-1 tat activity, HIV-1 inhibitors, and T cell activation effects. AIDS Res Hum Retroviruses 10, 295-301.

Blakely, K., Ketela, T., and Moffat, J. (2011). Pooled Lentiviral shRNA Screening for Functional Genomics in Mammalian Cells. Methods Mol Biol 781, 161-182.

Blasius, A. L., and Beutler, B. (2010). Intracellular toll-like receptors. Immunity 32, 305-315.

Caroff, M., and Karibian, D. (2003). Structure of *bacterial lipopolysaccharides*. Carbohydr Res 338, 2431-2447.

Carter, D., and Reed, S. G. (2010). Role of adjuvants in modeling the immune response. Curr Opin HIV AIDS 5, 409-413.

Chen, G. I., and Gingras, A.-C. (2007). Affinity-purification mass spectrometry (AP-MS) of serine/threonine phosphatases. Methods 42, 298-305.

Chow, J. C., Young, D. W., Golenbock, D. T., Christ, W. J., and Gusovsky, F. (1999). Toll-like receptor-4 mediates lipopolysaccharide-induced signal transduction. J Biol Chem 274, 10689-10692.

Deng, S., Zhu, S., Qiao, Y., Liu, Y. J., Chen, W., Zhao, G., and Chen, J. (2014). Recent advances in the role of toll-like receptors and TLR agonists in immunotherapy for human glioma. Protein Cell 12, 899-911.

Desroy, N., Denis, A., Oliveira, C., Atamanyuk, D., Briet, S., Faivre, F., Lefralliec, G., Bonvin, Y., Oxoby, M., Escaich, S., et a. (2013). Novel *HldE-K* Inhibitors Leading to Attenuated Gram Negative Bacterial Virulence. J Med Chem. 56, 1418-1430.

Ea, C.-K., Sun, L., Inoue, J.-I., and Chen, Z. J. (2004). TIFA activates IkappaB kinase (IKK) by promoting oligomerization and ubiquitination of TRAF6. Proc Natl Acad Sci USA 101, 15318-15323.

Edwards, J. C., Sedgwick, A. D., and Willoughby, D. A. (1981). The formation of a structure with the features of synovial lining by subcutaneous injection of air: an in vivo tissue culture system. J Pathol 134, 147-156.

Ferrao, R., Li, J., Bergamin, E., and Wu, H. (2012). Structural insights into the assembly of large oligomeric signalosomes in the Toll-like receptor-interleukin-1 receptor superfamily. Sci Signal 5, re3.

Franchi, L., Amer, A., Body-Malapel, M., Kanneganti, T.-D., Ozoren, N., Jagirdar, R., Inohara, N., Vandenabeele, P., Bertin, J., Coyle, A., et al. (2006). Cytosolic flagellin requires Ipaf for activation of caspase-1 and interleukin 1 beta in *salmonella*-infected macrophages. Nat Immunol 7, 576-582.

Girardin, S. E., Boneca, I. G., Carneiro, L. A. M., Antignac, A., Jéhanno, M., Viala, J., Tedin, K., Taha, M.-K., Labigne, A., Zähringer, U., et al. (2003). Nod1 detects a unique muropeptide from gram-negative bacterial peptidoglycan. Science 300, 1584-1587.

Girardin, S. E., Sansonetti, P. J., and Philpott, D. J. (2002). Intracellular vs extracellular recognition of pathogens—common concepts in mammals and flies. Trends Microbiol 10, 193-199.

Hagar, J. A., Powell, D. A., Aachoui, Y., Ernst, R. K., and Miao, E. A. (2013). Cytoplasmic LPS activates caspase-11: implications in TLR4-independent endotoxic shock. Science 341, 1250-1253.

Hara, H., Ishihara, C., Takeuchi, A., Imanishi, T., Xue, L., Morris, S. W., lnui, M., Takai, T., Shibuya, A., Saijo, S., et al. (2007). The adaptor protein CARD9 is essential for the activation of myeloid cells through ITAM-associated and Toll-like receptors. Nat Immunol 8, 619-629.

Herget, S., Toukach, P. V., Ranzinger, R., Hull, W. E., Knirel, Y. A., and von der Lieth, C.-W. (2008). Statistical analysis of the Bacterial Carbohydrate Structure Data Base (BCSDB): characteristics and diversity of bacterial carbohydrates in comparison with mammalian glycans. BMC Struct Biol 8, 35.

Hitchcock, P. J., and Brown, T. M. (1983). Morphological heterogeneity among *Salmonella lipopolysaccharide* chemotypes in silver-stained polyacrylamide gels. Journal of bacteriology 154, 269-277.

Huang, C.-C. F., Weng, J.-H., Wei, T.-Y. W., Wu, P.-Y. G., Hsu, P.-H., Chen, Y.-H., Wang, S.-C., Qin, D., Hung, C.-C., Chen, S.-T., et al. (2012). Intermolecular binding between TIFA-FHA and TIFA-pT mediates tumor necrosis factor alpha stimulation and NF-κB activation. Mol Cell Biol 32, 2664-2673.

Iwasaki, A and Medzhitov, R. (2010). Regulation of adaptive immunity by the innate immune system. *Science* 327, 291-295 (2010).

Kanamori, M., Suzuki, H., Saito, R., Muramatsu, M., and Hayashizaki, Y. (2002). T2BP, a novel TRAF2 binding protein, can activate NF-kappaB and AP-1 without TNF stimulation. Biochem Biophys Res Commun 290, 1108-1113.

Kawai, T., Takahashi, K., Sato, S., Coban, C., Kumar, H., Kato, H., Ishii, K. J., Takeuchi, O, and Akira, S. (2005). IPS-1, an adaptor triggering RIG-I- and Mda5-mediated type I interferon induction. Nat Immunol 6, 981-988.

Kayagaki, N., Wong, M. T., Stowe, I. B., Ramani, S. R., Gonzalez, L. C., Akashi-Takamura, Noncanonical inflammasome activation by intracellular LPS independent of TLR4. Science 341, 1246-1249.

Ketela, T., Heisler, L. E., Brown, K. R., Ammar, R., Kasimer, D., Surendra, A., Ericson, E., Blakely, K., Karamboulas, D., Smith, A. M., et al. (2011). A comprehensive platform for highly multiplexed mammalian functional genetic screens. BMC Genomics 12, 213.

Kneidinger, B., Marolda, C., Graninger, M., Zamyatina, A., McArthur, F., Kosma, P., Valvano, M. A., and Messner, P. (2002). Biosynthesis pathway of ADP-L-glycerol-beta-D-manno-heptose in *Escherichia coli*. Journal of bacteriology 184, 363-369.

Kobayashi, K., Inohara, N., Hernandez, L. D., Gálan, J. E., Núñez, G., Janeway, C. A., Medzhitov, R., and Flavell, R. A. (2002). RICK/Rip2/CARDIAK mediates signalling for receptors of the innate and adaptive immune systems. Nature 416, 194-199.

Kofoed, E. M., and Vance, R. E. (2013). Blue native polyacrylamide gel electrophoresis to monitor inflammasome assembly and composition. Methods Mol Biol 1040, 169-183.

Kumar, H., Kawai, T., and Akira, S. (2011). Pathogen recognition by the innate immune system. Int Rev Immunol 30, 16-34.

Loutet, S. A., Flannagan, R. S., Kooi, C., Sokol, P. A., and Valvano, M. A. (2006). A complete lipopolysaccharide inner core oligosaccharide is required for resistance of. *Burkholderia cenocepacia* to antimicrobial peptides and bacterial survival in vivo. Journal of bacteriology 188, 2073-2080.

Macia, E., Ehrlich, M., Massol, R., Boucrot, E., Brunner, C., and Kirchhausen, T. (2006). Dynasore, a cell-permeable inhibitor of dynamin. Dev Cell 10, 839-850.

Maisonneuve, C., Bertholet, S., Philpott, D. J., and De Gregorio, E. (2014). Unleashing the potential of NOD- and Toll-like agonists as vaccine adjuvants. Proc Natl Acad Sci USA 111, 12294-12299.

Malott, R. J., Keller, B. O., Gaudet, R. G., McCaw, S. E., Lai, C. C. L., Dobson-Belaire, W. N., Hobbs, J. L., St Michael, F., Cox, A. D., Moraes, T. F., et al. (2013). *Neisseria gonorrhoeae*-derived heptose elicits an innate immune response and drives HIV-1 expression. Proc Natl Acad Sci USA 110, 10234-10239.

Marcotte, R., Brown, K. R., Suarez, F., Sayad, A., Karamboulas, K., Krzyzanowski, P. M., Sircoulomb, F., Medrano, M., Fedyshyn, Y., Koh, J. L. Y., et al. (2012). Essential gene profiles in breast, pancreatic, and ovarian cancer cells. Cancer Discov 2, 172-189.

Masumoto, J., Yang, K., Varambally, S., Hasegawa, M., Tomlins, S. A., Qiu, S., Fujimoto, Y., Kawasaki, A., Foster, S. J., Horie, Y., et al. (2006). Nod1 acts as an intracellular receptor to stimulate chemokine production and neutrophil recruitment in vivo. J Exp Med 203, 203-213.

McCaw, S. E., Schneider, J., Liao, E. H., Zimmermann, W., and Gray-Owen, S. D. (2003). Immunoreceptor tyrosine-based activation motif phosphorylation during engulfment of *Neisseria gonorrhoeae* by the neutrophil-restricted CEACAM3 (CD66d) receptor. Mol Microbiol 49, 623-637.

Medzhitov, R. (2007). Recognition of microorganisms and activation of the immune response. Nature 449, 819-826.

Medzhitov, R. (2009). Approaching the asymptote: 20 years later. Immunity 30, 766-775.

Medzhitov, R., Preston-Hurlburt, P., Kopp, E., Stadlen, A., Chen, C., Ghosh, S., and Janeway, C. A. (1998). MyD88 is an adaptor protein in the hToll/IL-1 receptor family signaling pathways. Mol Cell 2, 253-258.

Meylan, E., Curran, J., Hofmann, K., Moradpour, D., Binder, M., Bartenschlager, R., and Tschopp, J. (2005). Cardif is an adaptor protein in the RIG-I antiviral pathway and is targeted by hepatitis C virus. Nature 437, 1167-1172.

Moffat, J., Grueneberg, D. A., Yang, X., Kim, S. Y., Kloepfer, A. M., Hinkle, G., Piqani, B., Eisenhaure, T. M., Luo, B., Grenier, J. K., et al. (2006). A lentiviral RNAi library for human and mouse genes applied to an arrayed viral high-content screen. Cell 124, 1283-1298.

Moreno, S. (2012). Anti-latency agents to purge HIV reservoirs. Retrovirology 9, 116.

Parvatiyar, K., Zhang, Z., Teles, R. M., Ouyang, S., Jiang, Y., Iyer, S. S., Zaver, S. A., Schenk, M., Zeng, S., Zhong, W., et al. (2012). The helicase DDX41 recognizes the bacterial secondary messengers cyclic di-GMP and cyclic di-AMP to activate a type I interferon immune response. Nat Immunol 13, 1155-1161.

Plant, L., Sundqvist, J., Zughaier, S., Lövkvist, L., Stephens, D. S., and Jonsson, A.-B. (2006). Lipooligosaccharide structure contributes to multiple steps in the virulence of *Neisseria meningitidis*. Infect Immun 74, 1360-1367.

Poteete, A. R., and Fenton, A. C. (1984). Lambda red-dependent growth and recombination of phage P22. Virology 134, 161-167.

Sander, L. E., Davis, M. J., Boekschoten, M. V., Amsen, D., Dascher, C. C., Ryffel, B., Swanson, J. A., Müller, M., and Blander, J. M. (2011). Detection of prokaryotic mRNA signifies microbial viability and promotes immunity. Nature 474, 385-389.

Schnaitman, C. A., and Klena, J. D. (1993). Genetics of lipopolysaccharide biosynthesis in enteric bacteria. Microbiol Rev 57, 655-682.

Seth, R. B., Sun, L., Ea, C.-K., and Chen, Z. J. (2005). Identification and characterization of MAVS, a mitochondrial antiviral signaling protein that activates NF-kappaB and IRF 3. Cell 122, 669-682.

Sun, L., Wu, J., Du, F., Chen, X., and Chen, Z. J. (2013). Cyclic GMP-AMP synthase is a cytosolic DNA sensor that activates the type I interferon pathway. Science 339, 786-791.

Takatsuna, H., Kato, H., Gohda, J., Akiyama, T., Moriya, A., Okamoto, Y., Yamagata, Y., Otsuka, M., Umezawa, K., Semba, K., et al. (2003). Identification of TIFA as an adapter protein that links tumor necrosis factor receptor-associated factor 6 (TRAF6) to interleukin-1 (IL-1) receptor-associated kinase-1 (IRAK-1) in IL-1 receptor signaling. J Biol Chem 278, 12144-12150.

van den Ent, F., and Löwe, J. (2006). RF cloning: a restriction-free method for inserting target genes into plasmids. J Biochem Biophys Methods 67, 67-74.

Weinberger, L. S., Burnett, J. C., Toettcher, J. E., Arkin, A. P., and Schaffer, D. V. (2005). Stochastic gene expression in a lentiviral positive-feedback loop: HIV-1 Tat fluctuations drive phenotypic diversity. Cell 122, 169-182.

Wu, J., Sun, L., Chen, X., Du, F., Shi, H., Chen, C., and Chen, Z. J. (2013). Cyclic GMP-AMP is an endogenous second messenger in innate immune signaling by cytosolic DNA. Science 339, 826-830.

Yoneyama, M., Kikuchi, M., Natsukawa, T., Shinobu, N., Imaizumi, T., Miyagishi, M., Taira, K., Akira, S., and Fujita, T. (2004). The RNA helicase RIG-I has an essential function in double-stranded RNA-induced innate antiviral responses. Nat Immunol 5, 730-737.

---

The invention claimed is:

1. A method of enhancing the immune responsiveness in a subject comprising administering an effective amount of a TIFA activator to a subject in need thereof.

2. The method according to claim 1 wherein the TIFA activator is heptose-1,7-bisphosphate.

3. The method according to claim 1 wherein the TIFA activator is D-glycero-D-manno-heptose-1α,7 bisphosphate or D-glycero-D-manno-heptose-1β,7 bisphosphate.

4. The method according to claim 1 further comprising administering an immunogen.

5. The method according to claim 4 wherein the immunogen is an antigen from a bacteria, virus, parasite or cancer cell.

6. The method according to claim 1 wherein the subject is a human.

7. A pharmaceutical composition for enhancing an immune response comprising an effective amount of a heptose-1,7-bisphosphate and a carrier.

8. The pharmaceutical composition according to claim 7 wherein the heptose-1,7-bisphosphate is D-glycero-D-manno-heptose-1α,7 bisphosphate or D-glycero-D-manno-heptose-1β,7 bisphosphate.

9. The pharmaceutical composition according to claim 7 further comprising an immunogen.

10. The pharmaceutical composition according to claim 9 wherein the immunogen is an antigen from a bacteria, virus, parasite or cancer cell.

* * * * *

SEQUENCE LISTING

```
<160> NUMBER OF SEQ ID NOS: 52

<210> SEQ ID NO 1
<211> LENGTH: 552
<212> TYPE: DNA
<213> ORGANISM: Homo sapiens

<400> SEQUENCE: 1
atgaccagtt ttgaagatgc tgacacagaa gagacagtaa cttgtctcca gatgacggtt    60
taccatcctg gccagttgca gtgtggaata tttcagtcaa taagttttaa cagagagaaa   120
ctcccttcca gcgaagtggt gaaatttggc cgaaattcca acatctgtca ttatactttt   180
caggacaaac aggtttcccg agttcagttt tctctgcagc tgtttaaaaa attcaacagc   240
tcagttctct cctttgaaat aaaaaatatg agtaaaaaga ccaatctgat cgtggacagc   300
agagagctgg gctacctaaa taaaatggac ctgccataca ggtgcatggt cagattcgga   360
gagtatcagt ttctgatgga gaaggaagat ggcgagtcat tggaattttt tgagactcaa   420 tttatttat  ctccaagatc actcttgcaa gaaaacaact ggccaccaca caggcccata   480
ccggagtatg gcacttattc gctctgctcc tcccaaagca gttctccgac agaaatggat   540
gaaaatgagt ca                                                       552

<210> SEQ ID NO 2
<211> LENGTH: 184
<212> TYPE: PRT
<213> ORGANISM: Homo sapiens

<400> SEQUENCE: 2

Met Thr Ser Phe Glu Asp Ala Asp Thr Glu Glu Thr Val Thr Cys Leu
1               5                   10                  15

Gln Met Thr Val Tyr His Pro Gly Gln Leu Gln Cys Gly Ile Phe Gln
            20                  25                  30

Ser Ile Ser Phe Asn Arg Glu Lys Leu Pro Ser Ser Glu Val Val Lys
        35                  40                  45

Phe Gly Arg Asn Ser Asn Ile Cys His Tyr Thr Phe Gln Asp Lys Gln
```

```
                50             55                  60
Val Ser Arg Val Gln Phe Ser Leu Gln Leu Phe Lys Lys Phe Asn Ser
65                  70                  75                  80

Ser Val Leu Ser Phe Glu Ile Lys Asn Met Ser Lys Lys Thr Asn Leu
                85                  90                  95

Ile Val Asp Ser Arg Glu Leu Gly Tyr Leu Asn Lys Met Asp Leu Pro
            100                 105                 110

Tyr Arg Cys Met Val Arg Phe Gly Glu Tyr Gln Phe Leu Met Glu Lys
            115                 120                 125

Glu Asp Gly Glu Ser Leu Glu Phe Phe Glu Thr Gln Phe Ile Leu Ser
            130                 135                 140

Pro Arg Ser Leu Leu Gln Glu Asn Asn Trp Pro Pro His Arg Pro Ile
145                 150                 155                 160

Pro Glu Tyr Gly Thr Tyr Ser Leu Cys Ser Ser Gln Ser Ser Ser Pro
                165                 170                 175

Thr Glu Met Asp Glu Asn Glu Ser
            180

<210> SEQ ID NO 3
<211> LENGTH: 594
<212> TYPE: DNA
<213> ORGANISM: Neisseria meningitidis

<400> SEQUENCE: 3
atgacgacat tacaagaacg cgttgccgcc cattttgccg aaagcatccg tgccaagcag      60
gaagccggaa agtattggtc gagccgacc gtacaggctg ccgagctgat gctgcaatgc     120
ctgatgaatg acggcaaaat cctggcctgc ggcaacggcg gttcggctgc cgacgcgcaa     180
cacttcgccg ccgaaatgac cggccgtttt gaaaaagaac gcatggaact cgccgctgtc     240
gcgctgacaa cagacacttc cgcgctgaca gccatcggca acgactacgg tttcgaccac     300
gtattcagca acaggtgcg cgcgctcgga cgtgcaggcg atgtattggt cggcattttcc     360 acctccggca attccgccaa cgtcatcgaa gccgtcaaag ccgcacacga acgcgatatg     420
cacgtcatcg ccttgaccgg ccgcgacggc ggcaaaatcg ccgccatact caaagacacc     480
gacgttttgc tcaacgttcc ccatccgcgc accgcccgta ttcaagaaaa ccacatcctg     540
ctgatacacg ccatgtgcga ctgtatcgac tccgtactgc tggaaggaat gtaa           594

<210> SEQ ID NO 4
<211> LENGTH: 579
<212> TYPE: DNA
<213> ORGANISM: Escherichia coli

<400> SEQUENCE: 4
atgtaccagg atcttattcg taacgaactg aacgaagcgg cggaaacgct ggctaacttt      60
ttaaaagatg acgccaatat tcacgccatt cagcgcgcgg cggtcctgtt agcagacagc     120
tttaaagccg gtggcaaagt gctttcctgc ggcaacggcg gttcccattg cgacgctatg     180
cactttgccg aagagttgac cggtcgctac cgtgaaaacc gtccgggcta cccggcgatt     240
gctatttctg acgttagtca tatttcctgc gtcggtaatg atttcggttt caatgatatt     300
ttctcccgct acgttgaagc ggtaggtcgc gaaggcgatg tactgctggg gatctccacc     360
tccggtaact ctgcaaacgt gatcaaagcg atcgcagcgg cgcgtgagaa gggaatgaaa     420
gtgatcaccc tgaccggtaa agacggcggc aaaatggctg gcacggcgga tatcgaaatt     480
cgcgtaccgc acttggatta tgccgaccgc attcaggaga ttcacattaa agtgatccat     540
```

```
atcctgatcc agttgattga aaaagagatg gttaagtaa                           579
```

<210> SEQ ID NO 5
<211> LENGTH: 972
<212> TYPE: DNA
<213> ORGANISM: Neisseria meningitidis

<400> SEQUENCE: 5

```
atgtccgcca agttccaaca agaaaccctc aaatcccgtt tcgcgcaagc caaagtcctg    60
gttgtcggcg acgtgatgct cgaccgctat tggttcggcg atgtgtcccg tatttcgccc   120
gaagcccccg tgccggtggc gaaaatcgga cgaatcgacc aacgcgcggg cggagcggca   180
aatgtcgcgc gcaacatcgc ttcgttgggc ggcagggcag ggctgttgtc cgtaaccggc   240
aacgacgaag ccgccgacgc gctcgatgcg ctgatggtgc aggacggcgt cgcctcctat   300
ctgatgcgcg acaaacaaat cgccaccacc gtcaaactgc gcgtcgtcgc ccgcaaccag   360
cagcttatcc gtcttgattt tgaagaacat cccaactgcg aagtgttgga acaaatcaag   420
cagaaatacc gcgaaatctt gcccgaatac gacgcaatca ttttttcaga ctacggcaaa   480
ggcggcctgt cgcatatctc cgatatgatc gattgggcga acacgccgg caaaaccgtc   540
ttaatcgacc ccaaaggcga cgattacgaa aaatatgtcg gtgcaactct gattacgcct   600
aaccgcgccg aattgaaaga gtggtcggc agttggaaaa acgaaagcga gctgaccgaa    660
aaagcgcaaa acctgcgccg ccacctcgac ctgaccgccg ttttactgac ccgaagcgaa   720
gaaggcatga ccttgttcag cgaaggcgaa ccgatttacc agcccacccg cgcccaagaa   780
gtttacgacg tatccggtgc gggtgacacc gtcattgccg gaatgggctt gggtttggcg   840
gcaggctgca ccatgcccga agccatgtac cttgccaata ctgcggccgg ggttgtcgtg   900
gcgaaactcg gtacggcggt ttgctcgttt gccgaattga tcaaggcatt gtcagggcaa   960
tcaacaatgt ag                                                        972
```

<210> SEQ ID NO 6
<211> LENGTH: 1434
<212> TYPE: DNA
<213> ORGANISM: Escherichia coli

<400> SEQUENCE: 6

```
atgaaagtaa cgctgccaga gtttgaacgt gcaggagtga tggtggttgg tgatgtgatg    60
ctggatcgtt actggtacgg cccccaccagt cgtatctcgc cggaagcgcc ggtgcccgtg   120
gttaaagtga ataccatcga agaacgtccg ggcggcgcgg ctaacgtggc gatgaatatc   180
gcttctctcg gtgctaatgc acgcctggtc gggttgacgg gcattgacga tgcagcgcgc   240
gcgctgagta aatctctggc cgacgtcaac gtcaaatgcg acttcgtttc tgtaccgacg   300
catccgacca ttaccaaatt acgggtactt tcccgcaacc aacagctgat ccgtctggat   360
tttgaagaag gttcgaagg tgttgatccg cagccgctgc acgagcggat taatcaggcg   420
ctgagttcga ttggcgcgct ggtgctttct gactacgcca aggtgcgct ggcaagcgta    480
cagcagatga tccaactggc gcgtaaagcg ggtgttccgg tgctgattga tccaaaaggt   540
accgattttg agcgctaccg cggcgctacg ctgttaacgc cgaatctctc ggaatttgaa   600
gctgttgtcg gtaaatgtaa gaccgaagaa gagattgttg agcgcggcat gaaactgatt   660
gccgattacg aactctcggc tctgttagtg acccgttccg aacagggtat gtcgctgctg   720
caaccgggta aagcgccgct gcatatgcca acccaagcgc aggaagtgta tgacgttacc   780
```

```
ggtgcgggcg acacggtgat tgcgtcctg gcggcaacgc tggcagcggg taattcgctg      840
gaagaagcct gcttctttgc caatgcggcg gctggcgtgg tggtcggcaa actgggaacc    900
tccacggttt cgccgatcga gctggaaaat gctgtacgtg gacgtgcaga tacaggcttt    960
ggcgtgatga ccgaagagga actgaagctg gccgtagcgg cagcgcgtaa acgtggtgaa   1020
aaagtggtga tgaccaacgg tgtctttgac atcctgcacg ccgggcacgt ctcttatctg   1080
gcaaatgccc gcaagctggg tgaccgcttg attgttgccg tcaacagcga tgcctccacc   1140
aaacggctga aggggattc cgcccggta aacccactcg aacagcgtat gattgtgctg     1200
ggcgcactgg aagcggtcga ctgggtagtg tcgtttgaag aggacacgcc gcagcgcttg   1260
atcgccggga tcttgccaga tctgctggtg aaaggcggcg actataaacc agaagagatt   1320
gccgggagta aagaagtctg gccaacggt ggcgaagtgt tggtgctcaa ctttgaagac    1380
ggttgctcga cgaccaacat catcaagaag atccaacagg ataaaaaagg ctaa         1434
```

<210> SEQ ID NO 7
<211> LENGTH: 52
<212> TYPE: DNA
<213> ORGANISM: Neisseria meningitidis

<400> SEQUENCE: 7

```
agctcggtac ccggggatcc tctagagaag ttacaatgag ccctttttaga gg           52
```

<210> SEQ ID NO 8
<211> LENGTH: 53
<212> TYPE: DNA
<213> ORGANISM: Neisseria meningitidis

<400> SEQUENCE: 8

```
acagctatga ccatgattac gccaagcttt ccgggcgcaa ggcgcgtgcc ttc           53
```

<210> SEQ ID NO 9
<211> LENGTH: 52
<212> TYPE: DNA
<213> ORGANISM: Neisseria meningitidis

<400> SEQUENCE: 9

```
agctcggtac ccggggatcc tctagaagaa ataccggctt cagaatttaa tc            52
```

<210> SEQ ID NO 10
<211> LENGTH: 52
<212> TYPE: DNA
<213> ORGANISM: Neisseria meningitidis

<400> SEQUENCE: 10

```
acagctatga ccatgattac gccaagctta ccgggctacg tcggctttga ac            52
```

<210> SEQ ID NO 11
<211> LENGTH: 49
<212> TYPE: DNA
<213> ORGANISM: Neisseria meningitidis

<400> SEQUENCE: 11

```
gaacctgccc aaaccaaagg aaacgcgcaa ccatcatcga tgaattgtg                49
```

<210> SEQ ID NO 12
<211> LENGTH: 45
<212> TYPE: DNA
<213> ORGANISM: Neisseria meningitidis

<400> SEQUENCE: 12

```
tttgccttgt cggaaatgcg gtatgtcaac cctgaagctt gcatg              45

<210> SEQ ID NO 13
<211> LENGTH: 49
<212> TYPE: DNA
<213> ORGANISM: Neisseria meningitidis

<400> SEQUENCE: 13
ttttactcaa aacaaaggaa accgaatcaa ccatcatcga tgaattgtg           49

<210> SEQ ID NO 14
<211> LENGTH: 47
<212> TYPE: DNA
<213> ORGANISM: Neisseria meningitidis

<400> SEQUENCE: 14
ttctttcaaa caaaattacc aatcgtgtca accctgaagc ttgcatg             47

<210> SEQ ID NO 15
<211> LENGTH: 23
<212> TYPE: DNA
<213> ORGANISM: Neisseria meningitidis

<400> SEQUENCE: 15
acctgcccaa accaaaggaa acg                                      23

<210> SEQ ID NO 16
<211> LENGTH: 24
<212> TYPE: DNA
<213> ORGANISM: Neisseria meningitidis

<400> SEQUENCE: 16
atggttttgc cttgtcggaa atgc                                     24

<210> SEQ ID NO 17
<211> LENGTH: 27
<212> TYPE: DNA
<213> ORGANISM: Neisseria meningitidis

<400> SEQUENCE: 17
aacatcgtca aagcacttaa tcaacgc                                  27

<210> SEQ ID NO 18
<211> LENGTH: 26
<212> TYPE: DNA
<213> ORGANISM: Neisseria meningitidis

<400> SEQUENCE: 18
cgtgttgtcc gtaaacgttg aagtag                                   26

<210> SEQ ID NO 19
<211> LENGTH: 60
<212> TYPE: DNA
<213> ORGANISM: Escherichia coli

<400> SEQUENCE: 19
ctgcattttg tctattacat ttatgctgaa ggatatcctc gtgtaggctg agctgcttc    60

<210> SEQ ID NO 20
<211> LENGTH: 60
<212> TYPE: DNA
<213> ORGANISM: Escherichia coli
```

```
<400> SEQUENCE: 20
ccggatgcgg cgtaaacgtc ttatccggcc tacgccagac catatgaata tcctccttag      60

<210> SEQ ID NO 21
<211> LENGTH: 60
<212> TYPE: DNA
<213> ORGANISM: Escherichia coli

<400> SEQUENCE: 21
tattatcgcg cgcaaatttt gaatctctca ggagacagga gtgtaggctg gagctgcttc      60

<210> SEQ ID NO 22
<211> LENGTH: 60
<212> TYPE: DNA
<213> ORGANISM: Escherichia coli

<400> SEQUENCE: 22
cctgccatgt acgaagcgag atctgtgaac cgctttccgg catatgaata tcctccttag      60

<210> SEQ ID NO 23
<211> LENGTH: 60
<212> TYPE: DNA
<213> ORGANISM: Escherichia coli

<400> SEQUENCE: 23
agaactcaac gcgctattgt tacaagagga agcctgacgg gtgtaggctg gagctgcttc      60

<210> SEQ ID NO 24
<211> LENGTH: 60
<212> TYPE: DNA
<213> ORGANISM: Escherichia coli

<400> SEQUENCE: 24
tcaatgaatg aagtttaaag gatgttagca tgttttacct catatgaata tcctccttag      60

<210> SEQ ID NO 25
<211> LENGTH: 23
<212> TYPE: DNA
<213> ORGANISM: Escherichia coli

<400> SEQUENCE: 25
tagcacctgc ccgtacttct cgc                                              23

<210> SEQ ID NO 26
<211> LENGTH: 23
<212> TYPE: DNA
<213> ORGANISM: Escherichia coli

<400> SEQUENCE: 26
agacgcgtca gcgtcgcatc agg                                              23

<210> SEQ ID NO 27
<211> LENGTH: 23
<212> TYPE: DNA
<213> ORGANISM: Escherichia coli

<400> SEQUENCE: 27
aggtgttgat ccgcagccgc tgc                                              23

<210> SEQ ID NO 28
<211> LENGTH: 22
<212> TYPE: DNA
<213> ORGANISM: Escherichia coli
```

```
<400> SEQUENCE: 28
acgacactac ccagtcgacc gc                                           22

<210> SEQ ID NO 29
<211> LENGTH: 25
<212> TYPE: DNA
<213> ORGANISM: Escherichia coli

<400> SEQUENCE: 29
gctgccgttg agcgagttat cctg                                         25

<210> SEQ ID NO 30
<211> LENGTH: 22
<212> TYPE: DNA
<213> ORGANISM: Escherichia coli

<400> SEQUENCE: 30
cttccgccag tcgtttcgcc cg                                           22

<210> SEQ ID NO 31
<211> LENGTH: 20
<212> TYPE: DNA
<213> ORGANISM: Homo sapiens

<400> SEQUENCE: 31
ttgaggtcaa tgaagggggtc                                             20

<210> SEQ ID NO 32
<211> LENGTH: 20
<212> TYPE: DNA
<213> ORGANISM: Homo sapiens

<400> SEQUENCE: 32
gaaggtgaag gtcggagtca                                              20

<210> SEQ ID NO 33
<211> LENGTH: 19
<212> TYPE: DNA
<213> ORGANISM: Homo sapiens

<400> SEQUENCE: 33
tcatggatga tggccaagt                                               19

<210> SEQ ID NO 34
<211> LENGTH: 20
<212> TYPE: DNA
<213> ORGANISM: Homo sapiens

<400> SEQUENCE: 34
gtcaaggagc tgcaggagat                                              20

<210> SEQ ID NO 35
<211> LENGTH: 20
<212> TYPE: DNA
<213> ORGANISM: Homo sapiens

<400> SEQUENCE: 35
aagcaacatc tggagaaggg                                              20

<210> SEQ ID NO 36
<211> LENGTH: 20
<212> TYPE: DNA
```

<213> ORGANISM: Homo sapiens

<400> SEQUENCE: 36
atgcagatca tcaccacagc                                                    20

<210> SEQ ID NO 37
<211> LENGTH: 20
<212> TYPE: DNA
<213> ORGANISM: Homo sapiens

<400> SEQUENCE: 37
gccagagggc tgattagaga                                                    20

<210> SEQ ID NO 38
<211> LENGTH: 20
<212> TYPE: DNA
<213> ORGANISM: Homo sapiens

<400> SEQUENCE: 38
tcagcctctt ctccttcctg                                                    20

<210> SEQ ID NO 39
<211> LENGTH: 20
<212> TYPE: DNA
<213> ORGANISM: Homo sapiens

<400> SEQUENCE: 39
gcaggtacag cgtacggttc                                                    20

<210> SEQ ID NO 40
<211> LENGTH: 20
<212> TYPE: DNA
<213> ORGANISM: Homo sapiens

<400> SEQUENCE: 40
cagcagagga acctccagtc                                                    20

<210> SEQ ID NO 41
<211> LENGTH: 20
<212> TYPE: DNA
<213> ORGANISM: Homo sapiens

<400> SEQUENCE: 41
agcactcctt ggcaaaactg                                                    20

<210> SEQ ID NO 42
<211> LENGTH: 20
<212> TYPE: DNA
<213> ORGANISM: Homo sapiens

<400> SEQUENCE: 42
cggaaggaac catctcactg                                                    20

<210> SEQ ID NO 43
<211> LENGTH: 20
<212> TYPE: DNA
<213> ORGANISM: Homo sapiens

<400> SEQUENCE: 43
ctcactgaga ctacatcagc                                                    20

<210> SEQ ID NO 44
<211> LENGTH: 20

```
<212> TYPE: DNA
<213> ORGANISM: Homo sapiens

<400> SEQUENCE: 44
tccagatcca caaccttcgc                                              20

<210> SEQ ID NO 45
<211> LENGTH: 20
<212> TYPE: DNA
<213> ORGANISM: Homo sapiens

<400> SEQUENCE: 45
ggtgaatggc acttgaaaca                                              20

<210> SEQ ID NO 46
<211> LENGTH: 21
<212> TYPE: DNA
<213> ORGANISM: Homo sapiens

<400> SEQUENCE: 46
ggcacaaaat ccagatgaaa g                                            21

<210> SEQ ID NO 47
<211> LENGTH: 20
<212> TYPE: DNA
<213> ORGANISM: Homo sapiens

<400> SEQUENCE: 47
aaaggcttct cagcctcctc                                              20

<210> SEQ ID NO 48
<211> LENGTH: 20
<212> TYPE: DNA
<213> ORGANISM: Homo sapiens

<400> SEQUENCE: 48
actgctcgag ctgcttacca                                              20

<210> SEQ ID NO 49
<211> LENGTH: 20
<212> TYPE: DNA
<213> ORGANISM: Homo sapiens

<400> SEQUENCE: 49
tcagattctg gagagagggc                                              20

<210> SEQ ID NO 50
<211> LENGTH: 17
<212> TYPE: DNA
<213> ORGANISM: Homo sapiens

<400> SEQUENCE: 50
ggtcgccagg tctcagg                                                 17

<210> SEQ ID NO 51
<211> LENGTH: 20
<212> TYPE: DNA
<213> ORGANISM: Homo sapiens

<400> SEQUENCE: 51
atatacagcc gctggctcac                                              20

<210> SEQ ID NO 52
```

```
<211> LENGTH: 20
<212> TYPE: DNA
<213> ORGANISM: Homo sapiens

<400> SEQUENCE: 52
gatatctgcg gctgatcctg                                              20
```